United States Patent [19]

Bonutti

[11] Patent Number: 5,667,520

[45] Date of Patent: *Sep. 16, 1997

[54] METHOD OF PERFORMING BALLOON DISSECTION

[75] Inventor: Peter M. Bonutti, Effingham, Ill.

[73] Assignee: General Surgical Innovations, Inc., Palo Alto, Calif.

[ * ] Notice: The term of this patent shall not extend beyond the expiration date of Pat. No. 5,514,153.

[21] Appl. No.: 297,637

[22] Filed: Aug. 29, 1994

Related U.S. Application Data

[62] Division of Ser. No. 29,695, Mar. 11, 1993, Pat. No. 5,345,927, which is a division of Ser. No. 631,740, Dec. 18, 1990, Pat. No. 5,197,971, which is a continuation-in-part of Ser. No. 609,341, Nov. 5, 1990, abandoned, and Ser. No. 487,645, Mar. 2, 1990, Pat. No. 5,331,975.

[51] Int. Cl.$^6$ .............................. A61B 1/32; A61M 29/02
[52] U.S. Cl. .............. 606/190; 606/192; 600/207; 600/204
[58] Field of Search ............... 606/192, 193, 606/196, 198, 190; 604/105, 106; 600/207, 204

[56] References Cited

U.S. PATENT DOCUMENTS

| | | |
|---|---|---|
| 1,863,057 | 6/1932 | Innes . |
| 1,909,967 | 5/1933 | Jones . |
| 2,854,983 | 10/1958 | Baskin .................................. 604/96 |
| 3,397,699 | 8/1968 | Kohl . |
| 3,495,586 | 2/1970 | Regenbogen . |
| 4,295,464 | 10/1981 | Shihata .............................. 606/192 X |
| 4,312,353 | 1/1982 | Shahbabian ........................ 606/192 |
| 4,572,186 | 2/1986 | Gould et al. . |
| 4,585,000 | 4/1986 | Hershenson . |
| 4,608,965 | 9/1986 | Anspach, Jr. et al. . |
| 4,921,478 | 5/1990 | Solano et al. . |
| 4,954,126 | 9/1990 | Wallsten . |
| 4,998,539 | 3/1991 | Delsanti . |
| 5,041,093 | 8/1991 | Chu . |
| 5,122,122 | 6/1992 | Allgood . |
| 5,514,091 | 5/1996 | Yoon ................................... 604/101 |

FOREIGN PATENT DOCUMENTS

| | | | |
|---|---|---|---|
| 2580504 | 10/1986 | France .............................. 606/200 |
| 1323090 | 7/1987 | U.S.S.R. . |

*Primary Examiner*—Michael H. Thaler
*Attorney, Agent, or Firm*—Lyon & Lyon LLP

[57] ABSTRACT

A retractor for use in arthroscopic surgery. The retractor has a mechanical expanding portion for expanding against sub-surface tissues when the retractor is in use. The retractor also has a fluid-operated expanding portion, which may be independently controllable, for expanding against sub-surface tissues when the retractor is in use. The retractor is inserted through a small percutaneous opening, expanded in sub-surface tissues without significantly damaging the tissue, then collapsed after use for removal. The retractor can be manipulated to allow the surgeon to push or pull or lever on tissue. The retractor can be hollow like a cannula to permit the passage of one or more surgical devices through the retractor, with a side portal into the center of the retractor.

8 Claims, 23 Drawing Sheets

Fig.33

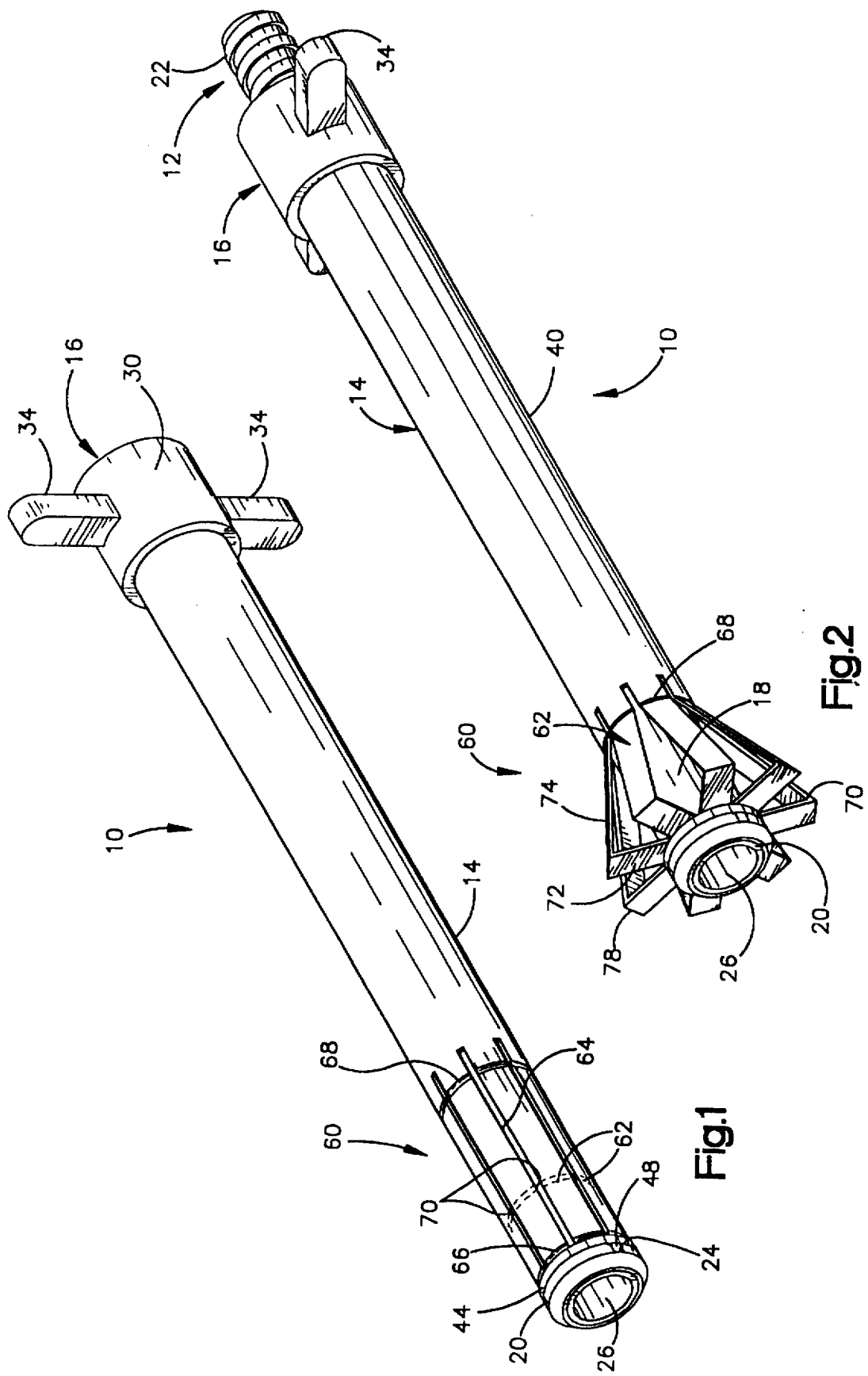

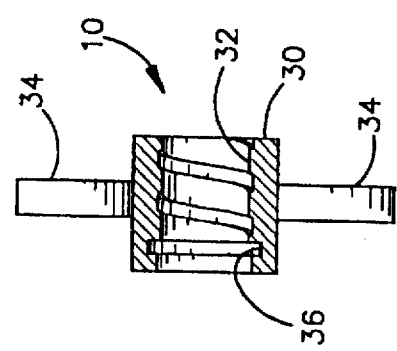
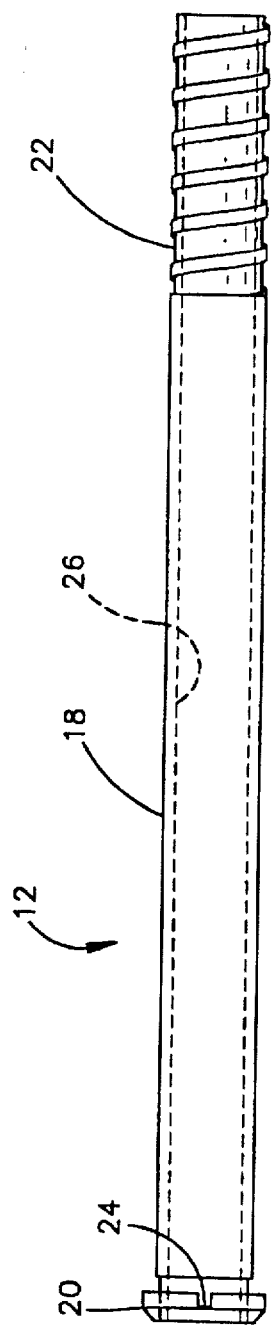
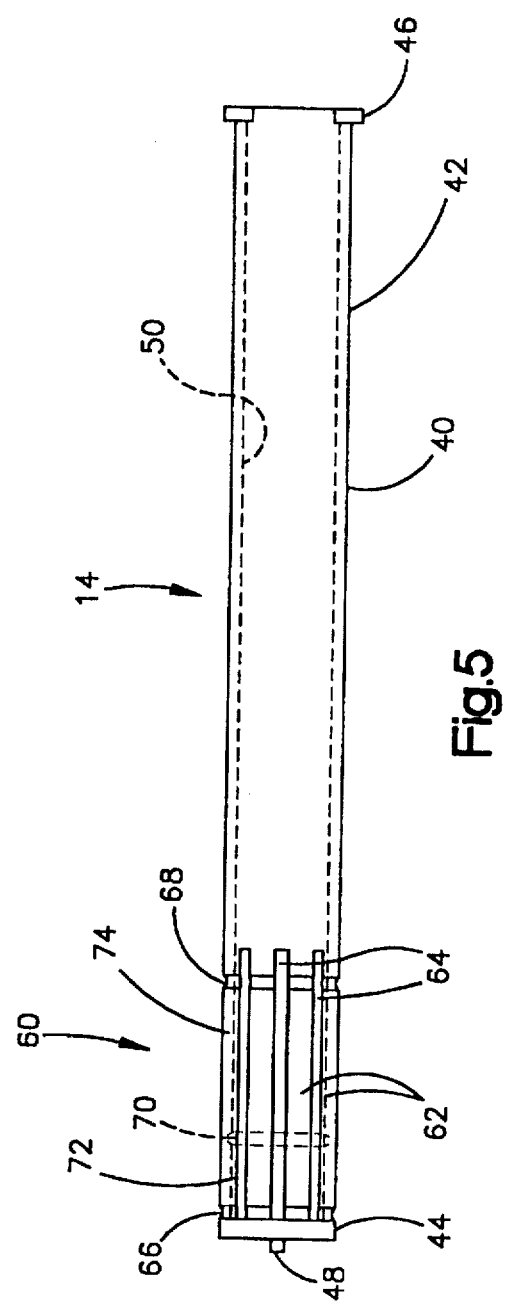

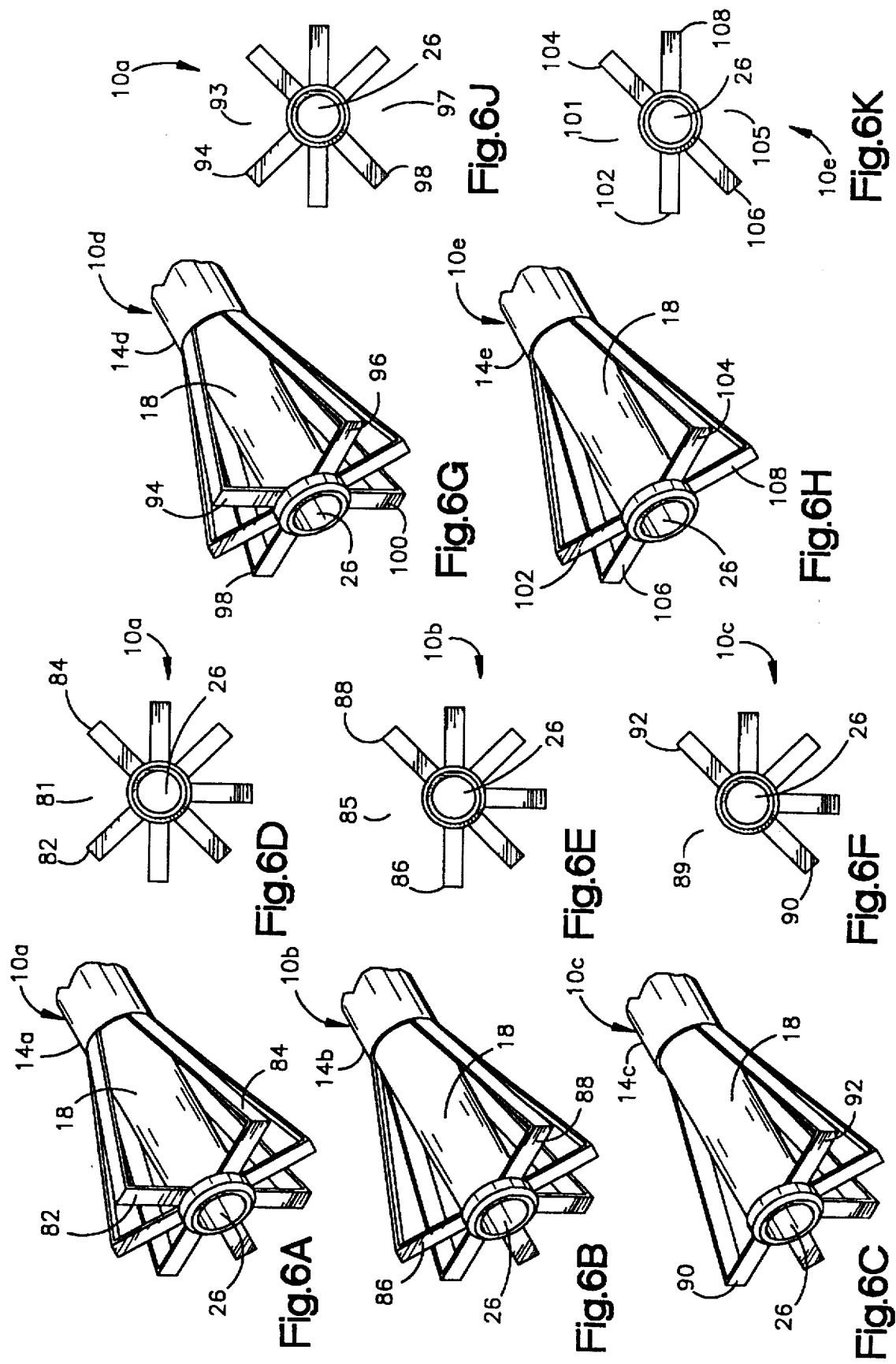

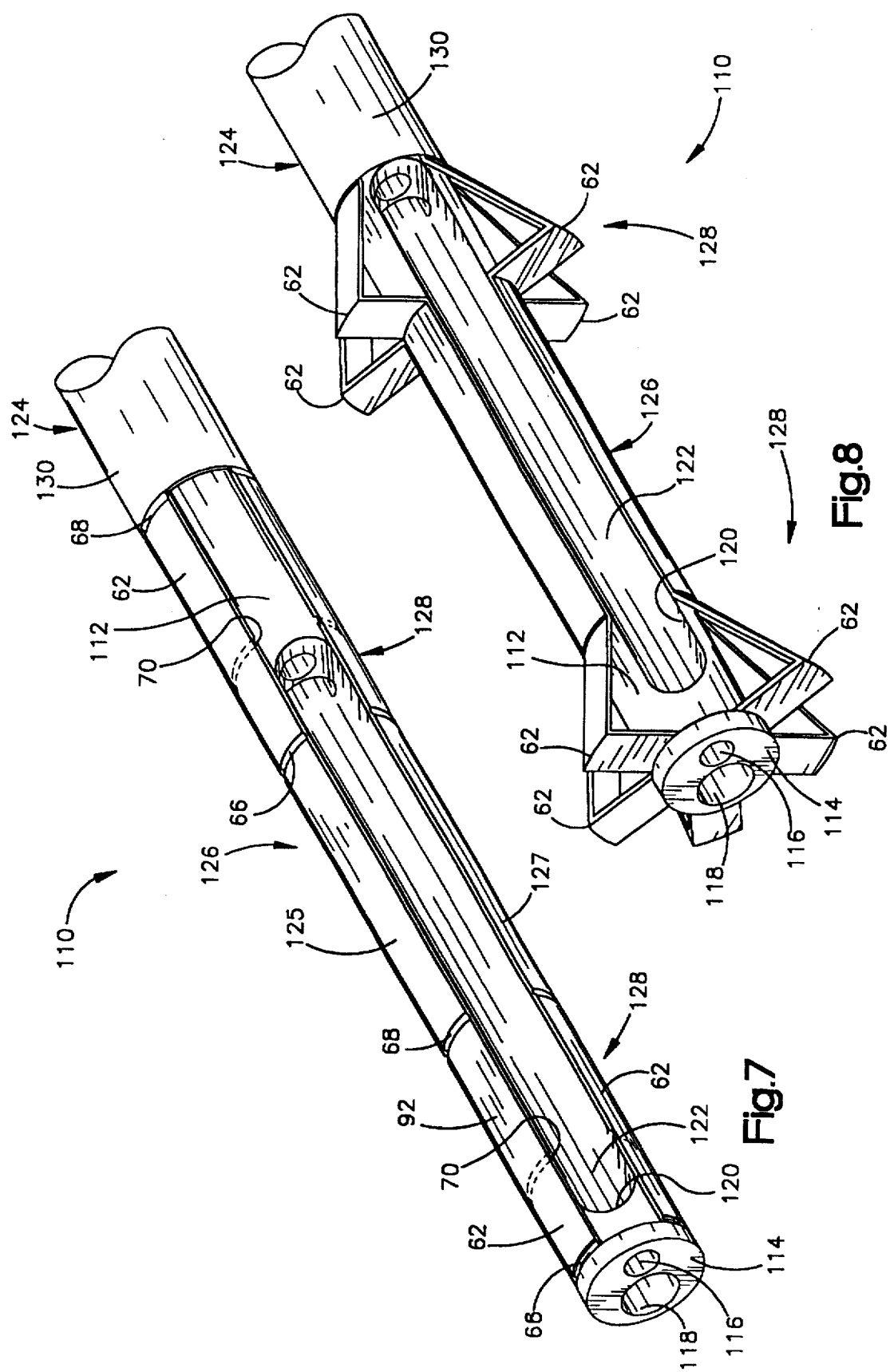

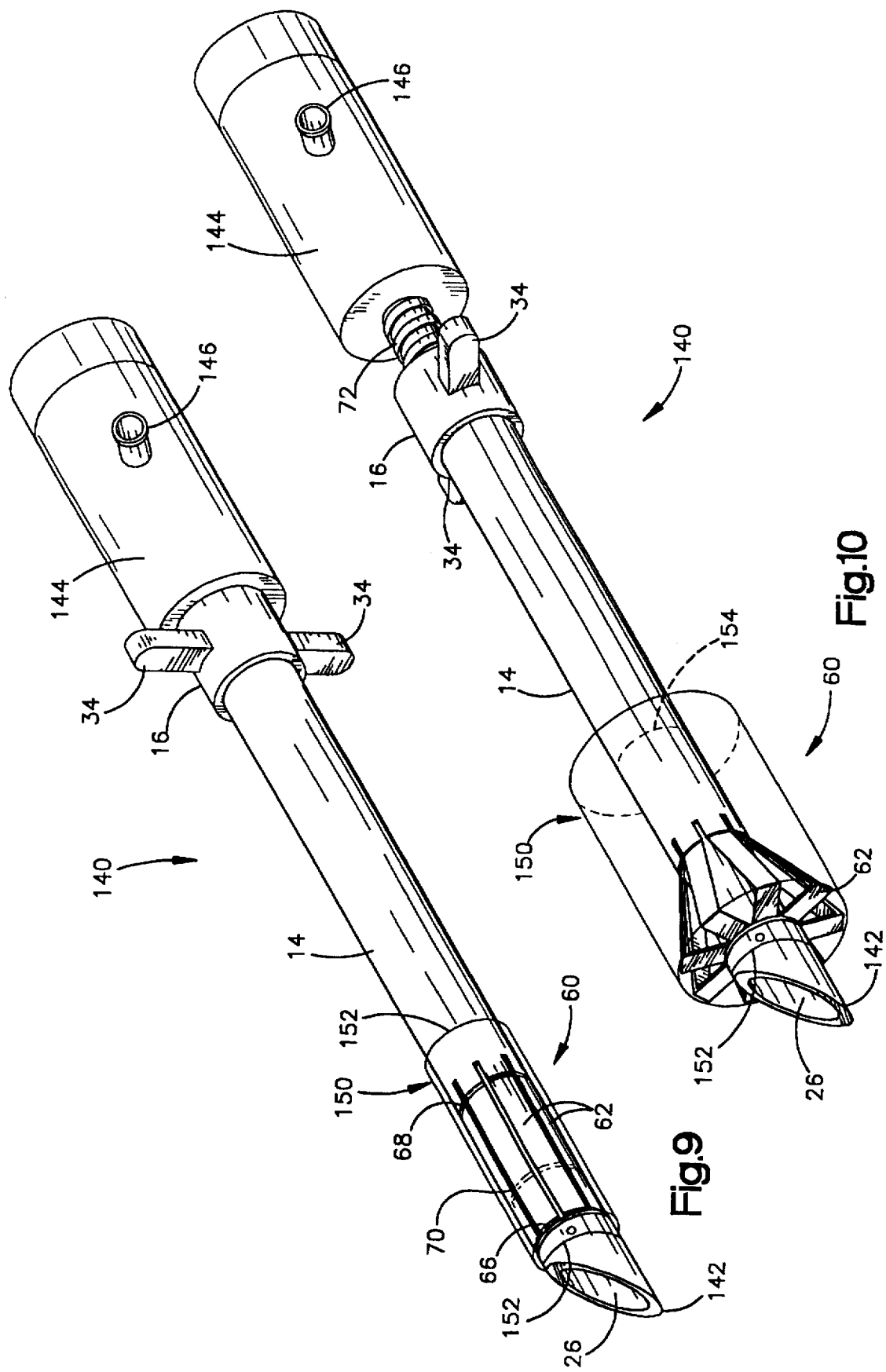

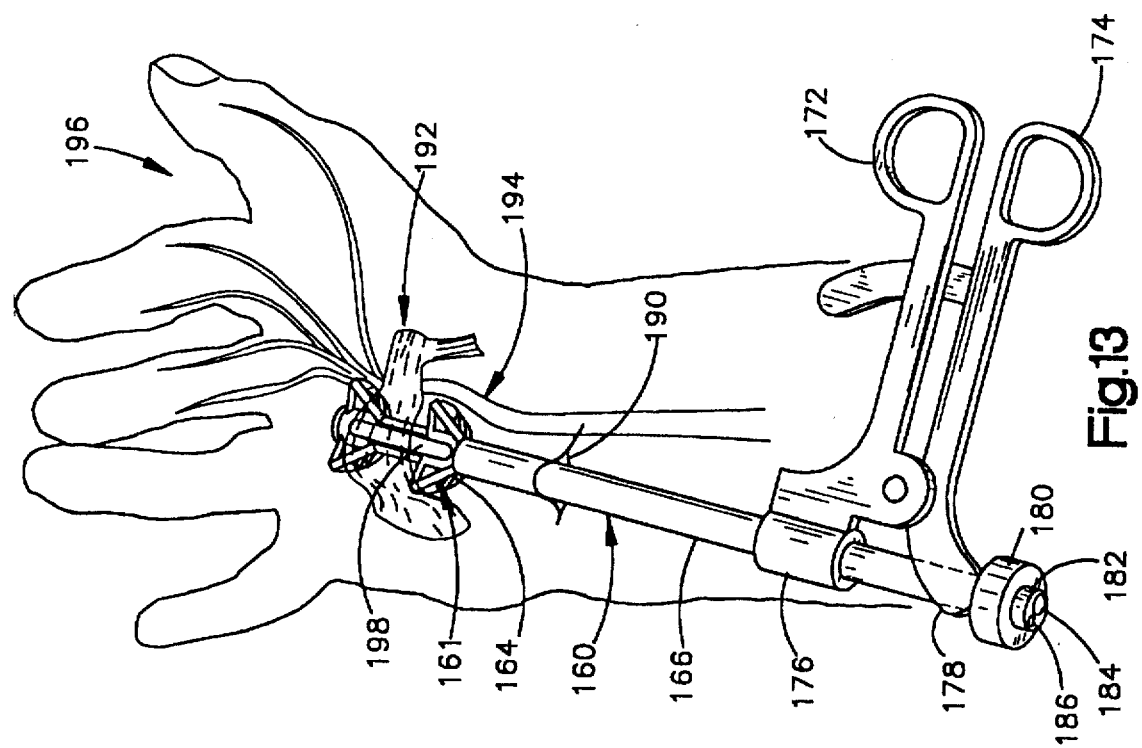
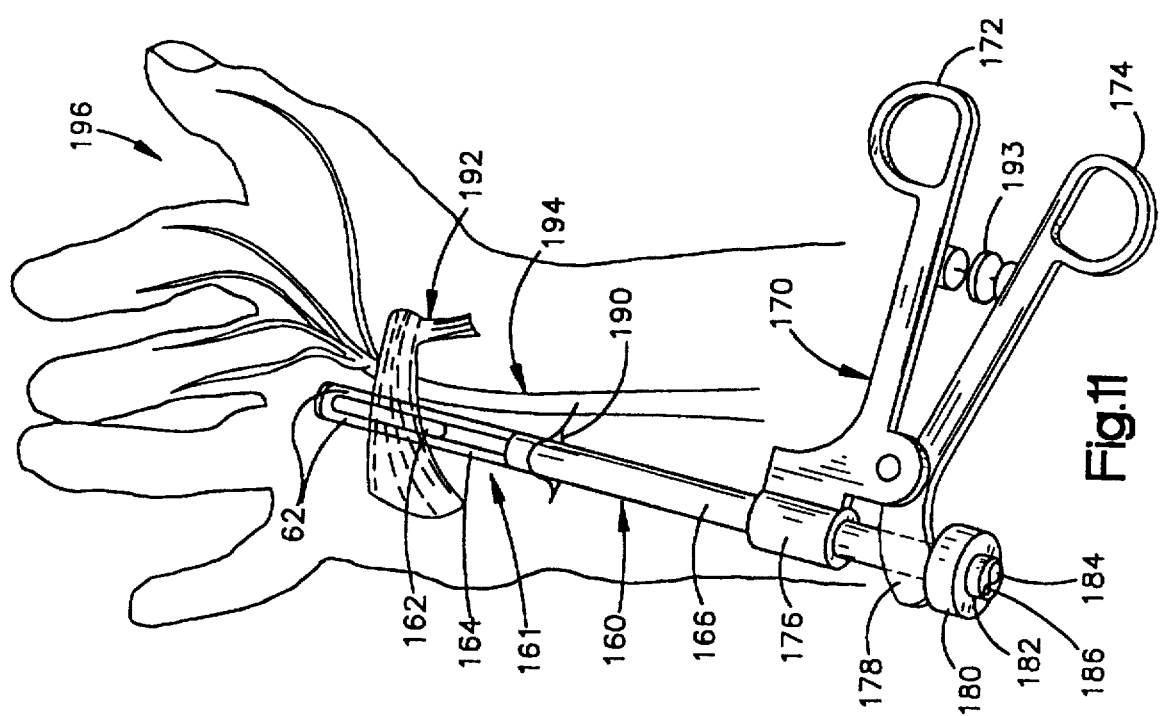

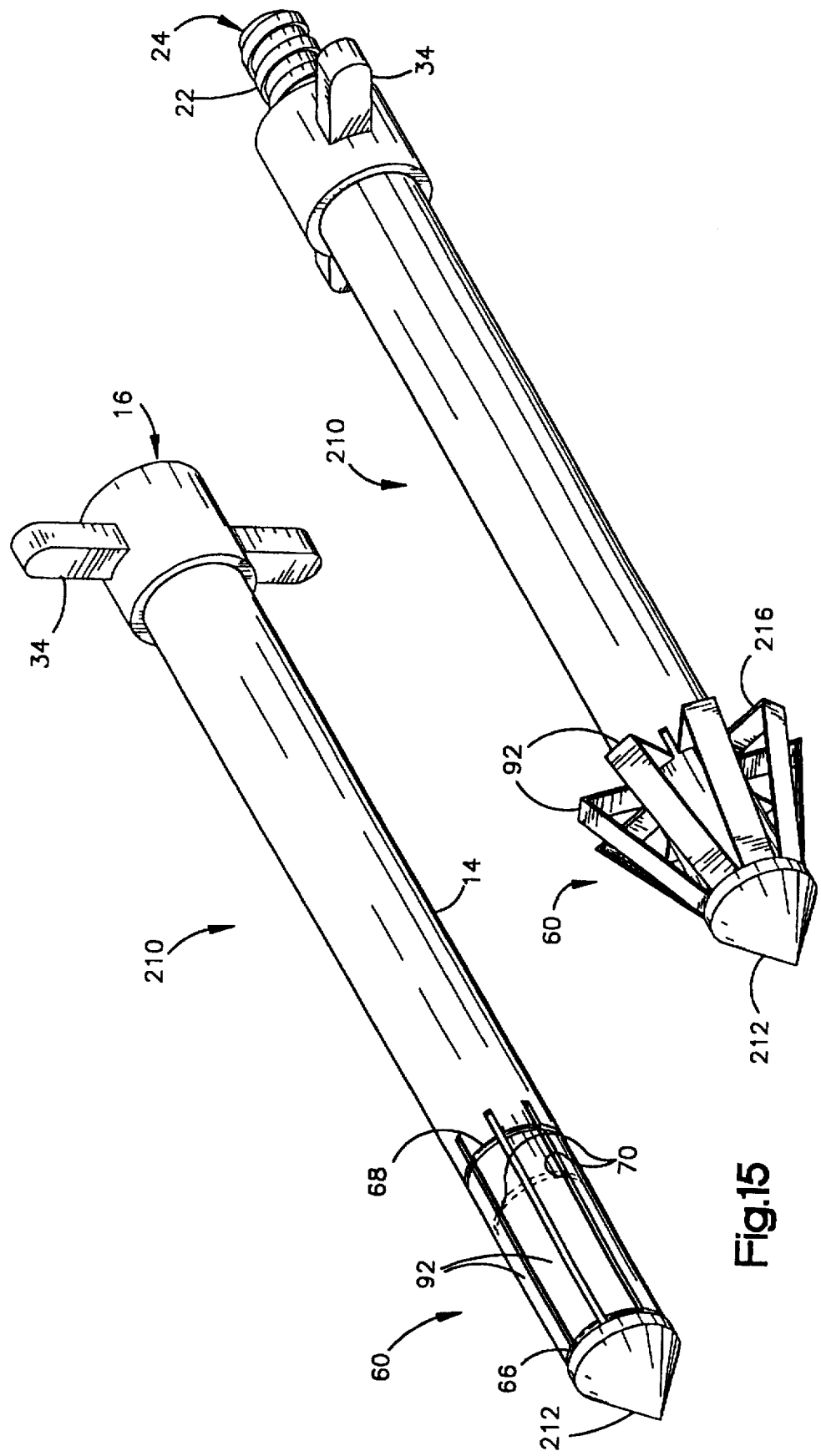

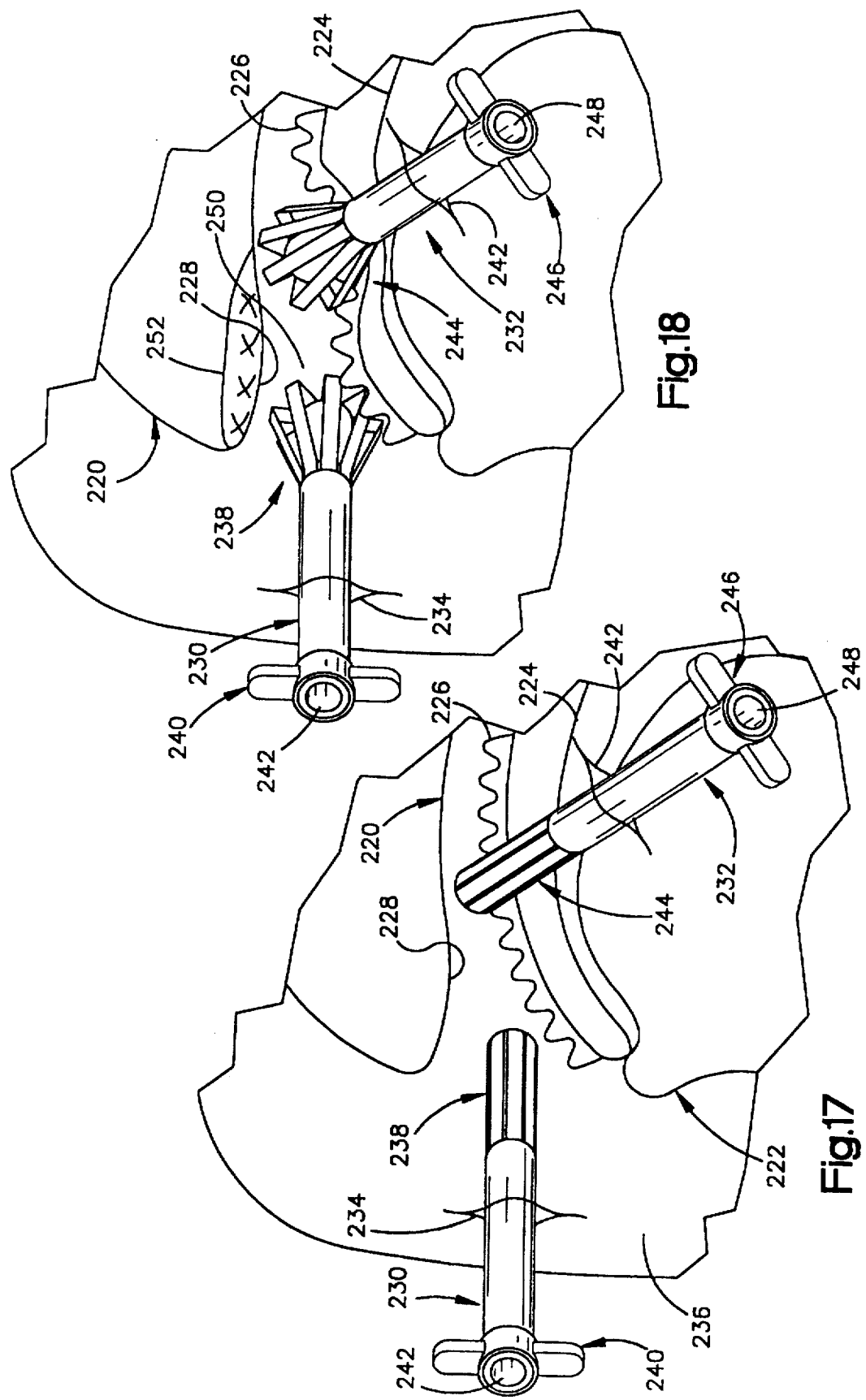

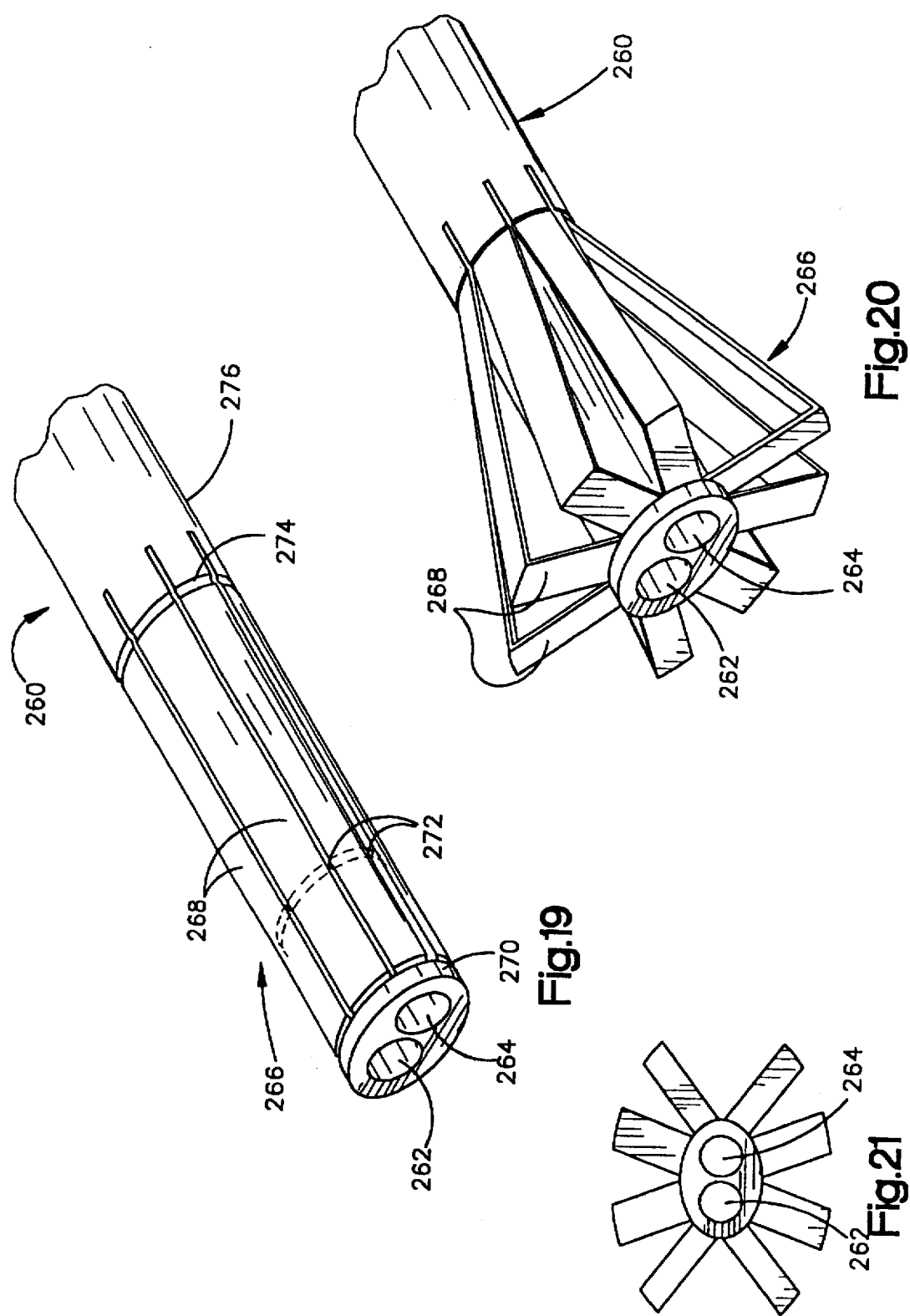

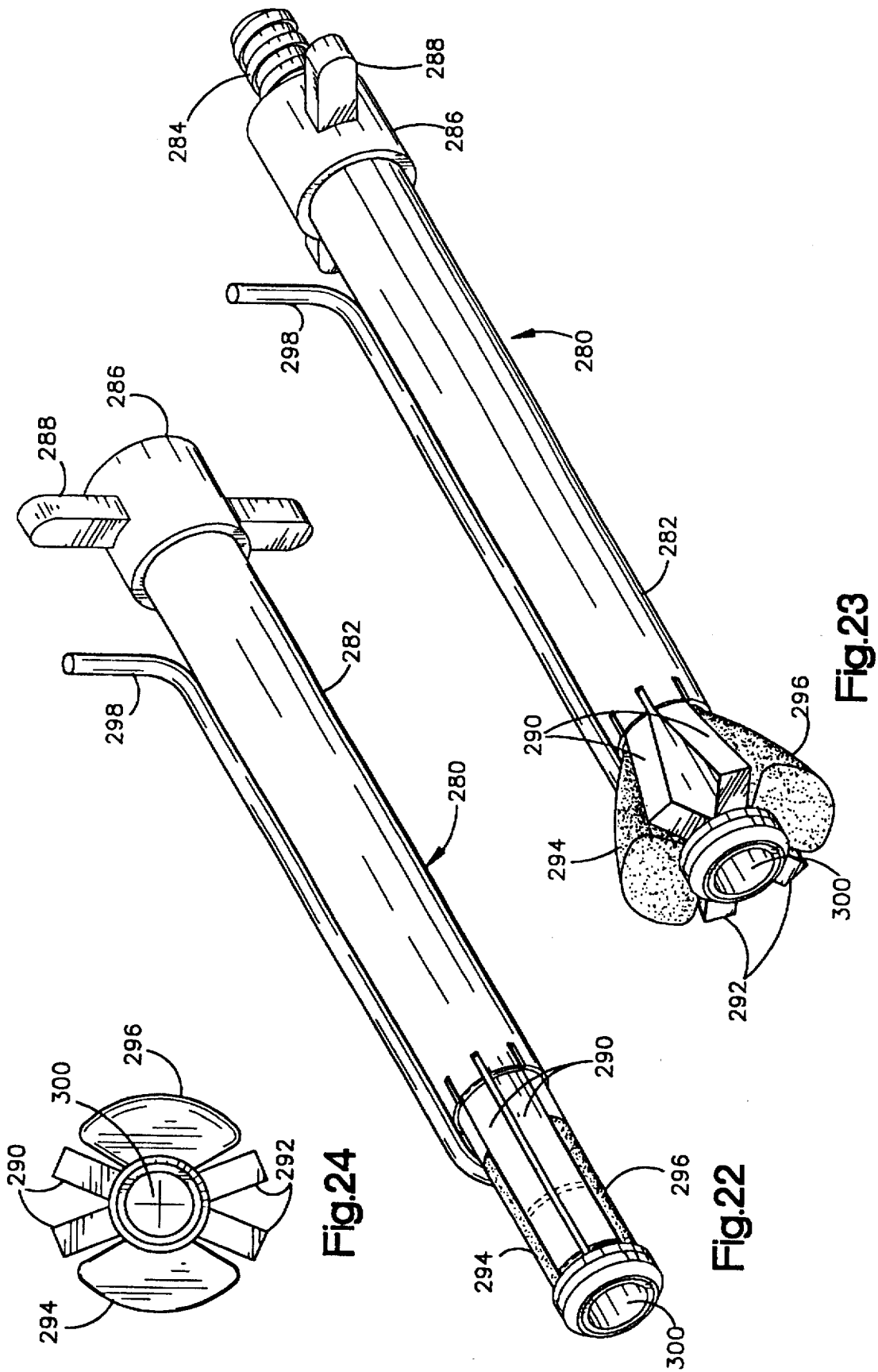

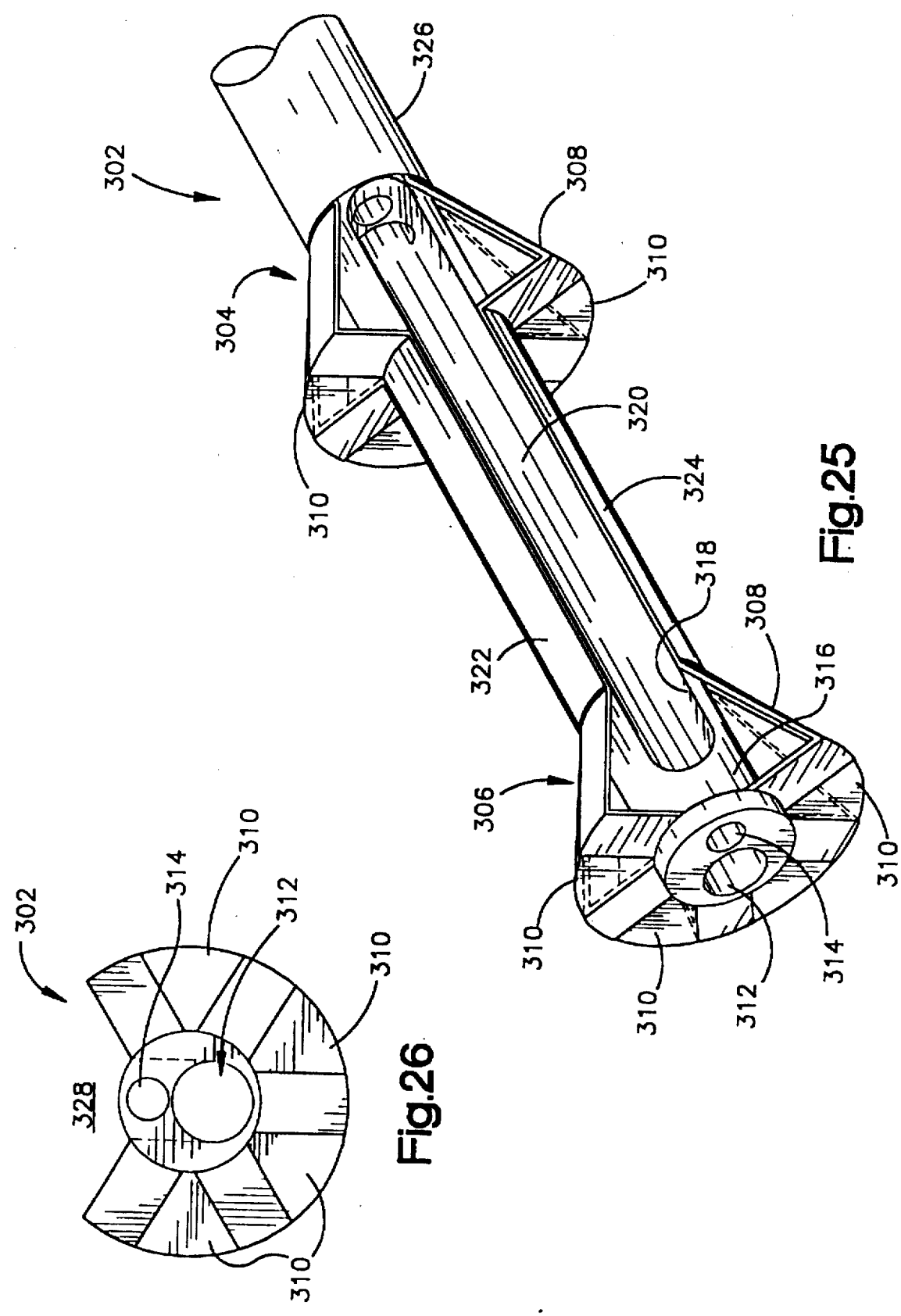

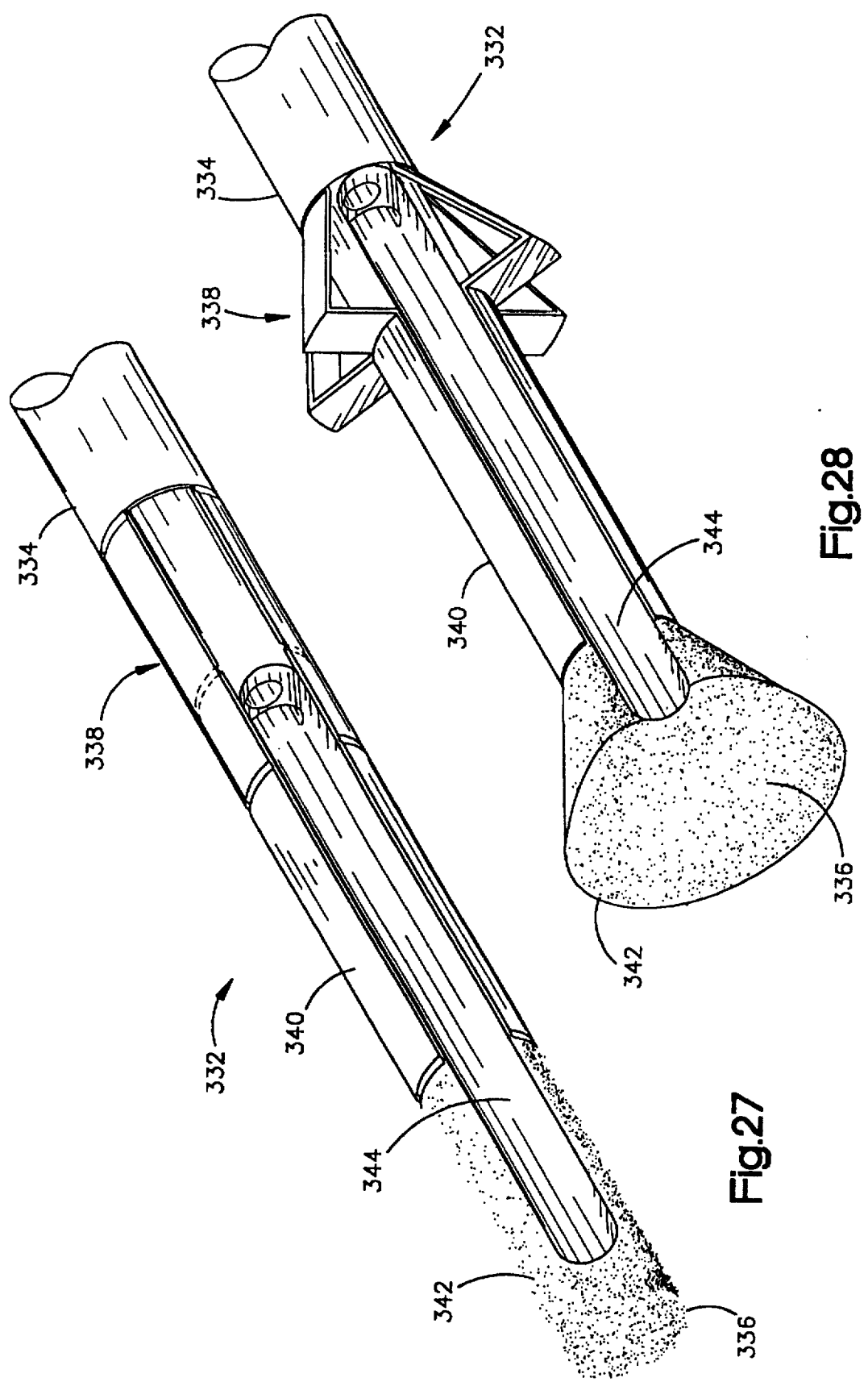

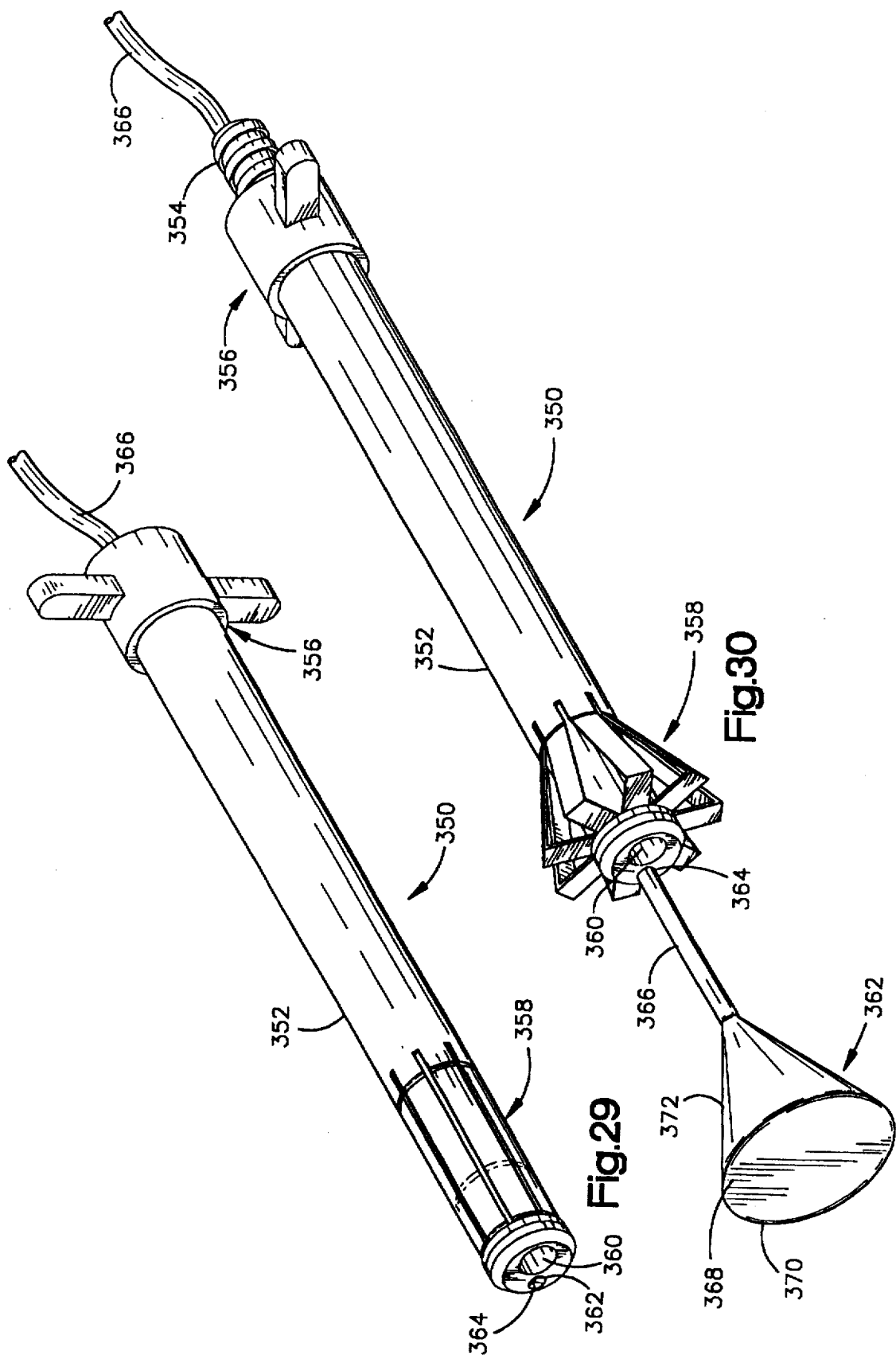

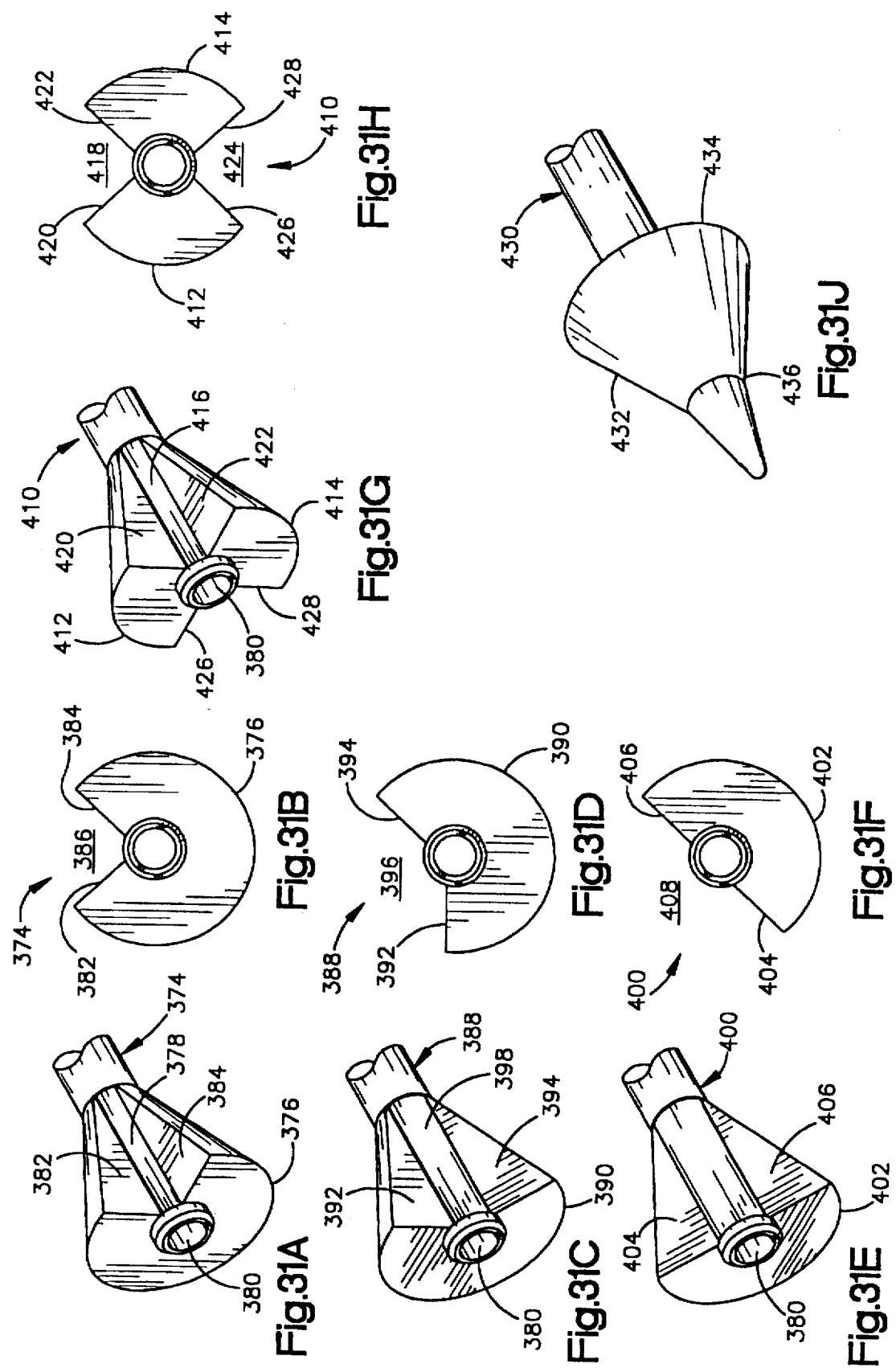

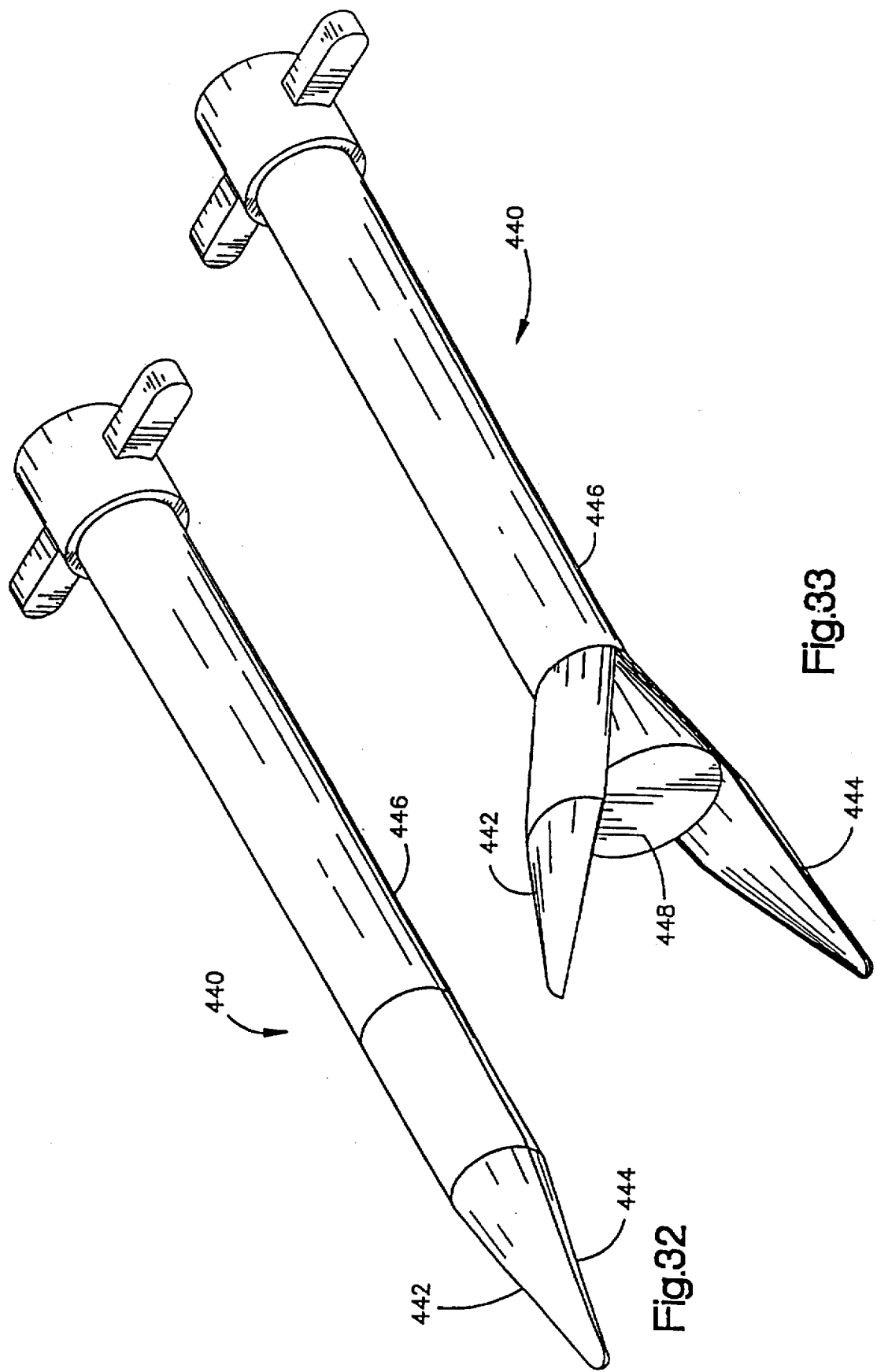

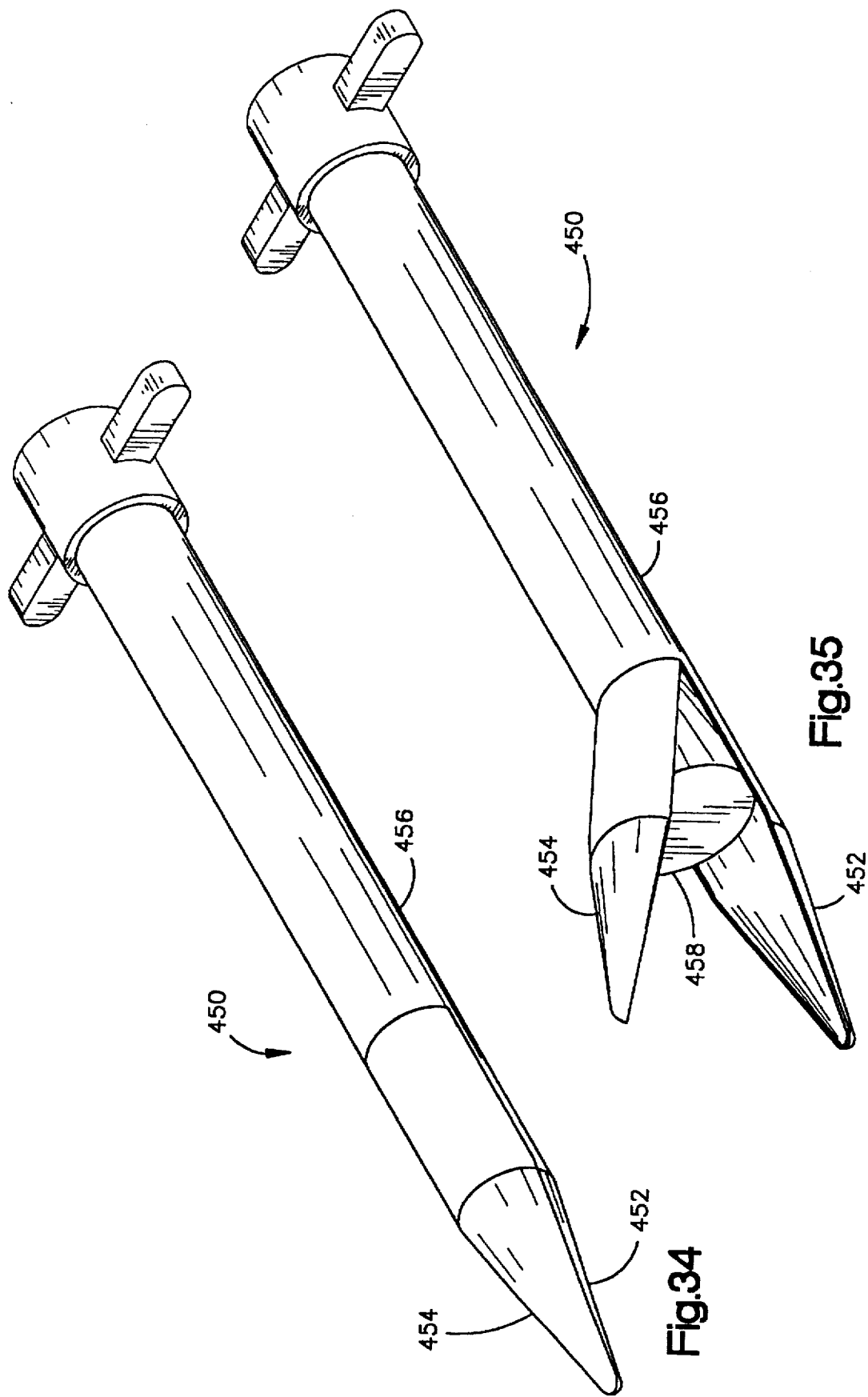

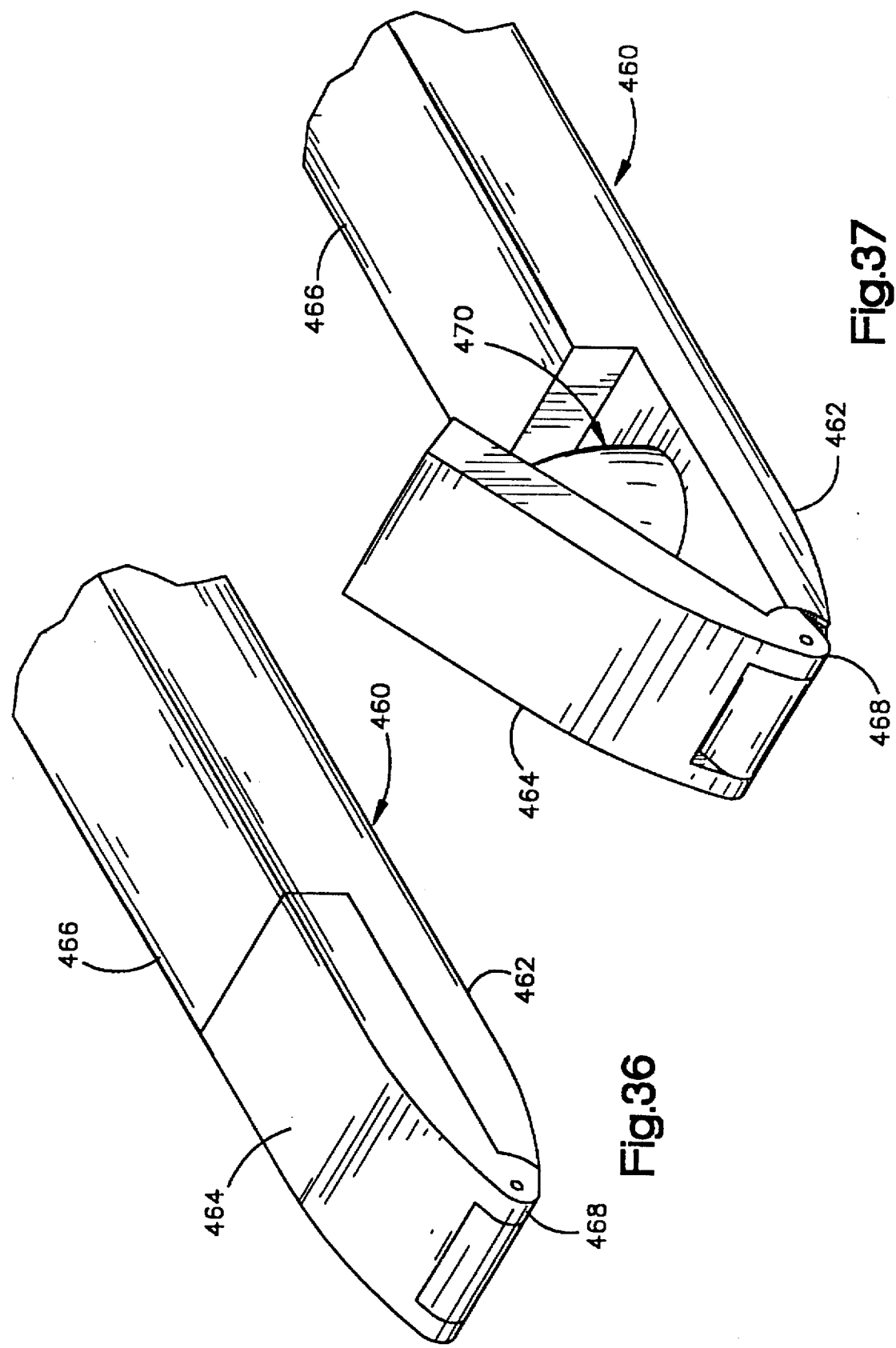

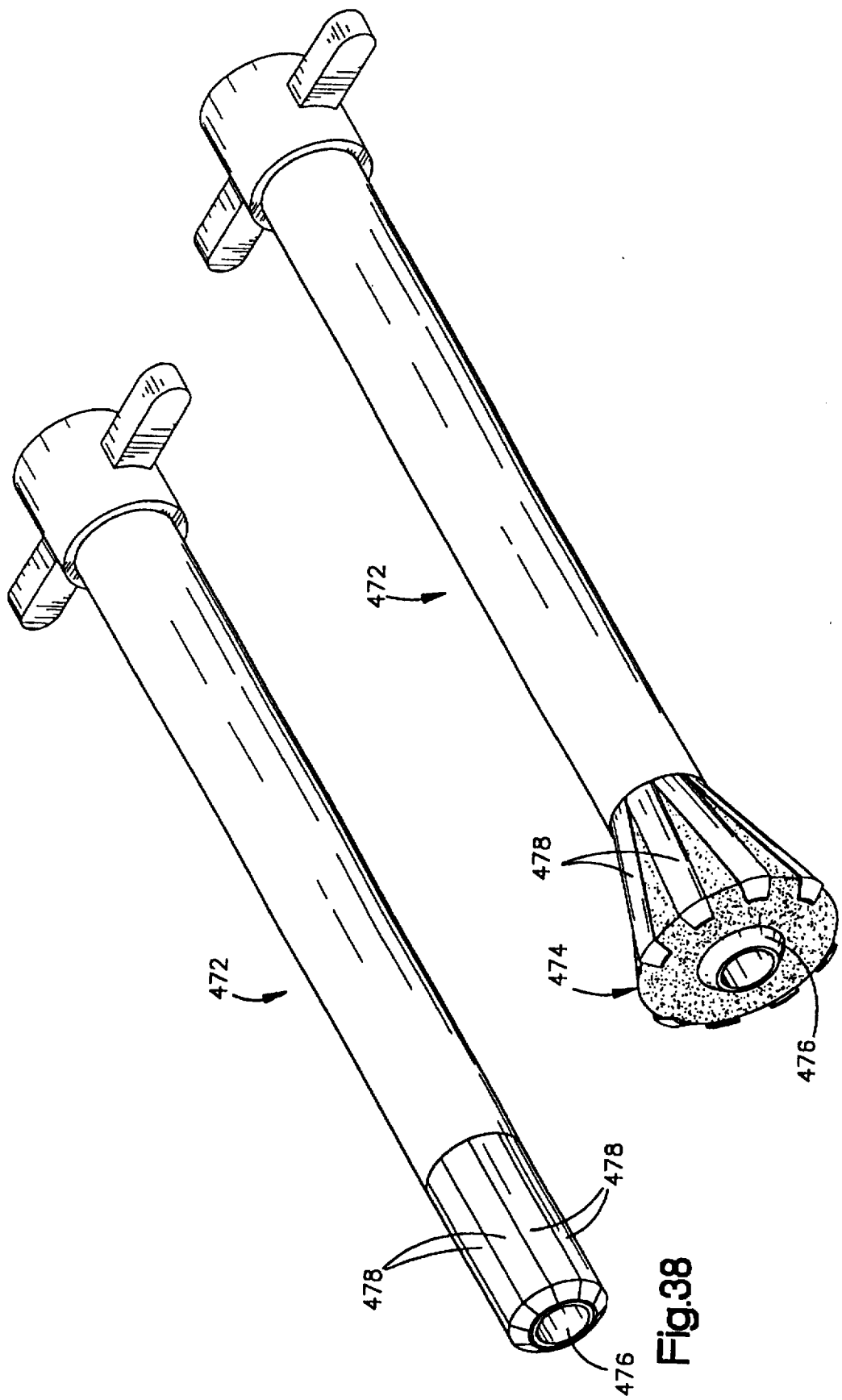

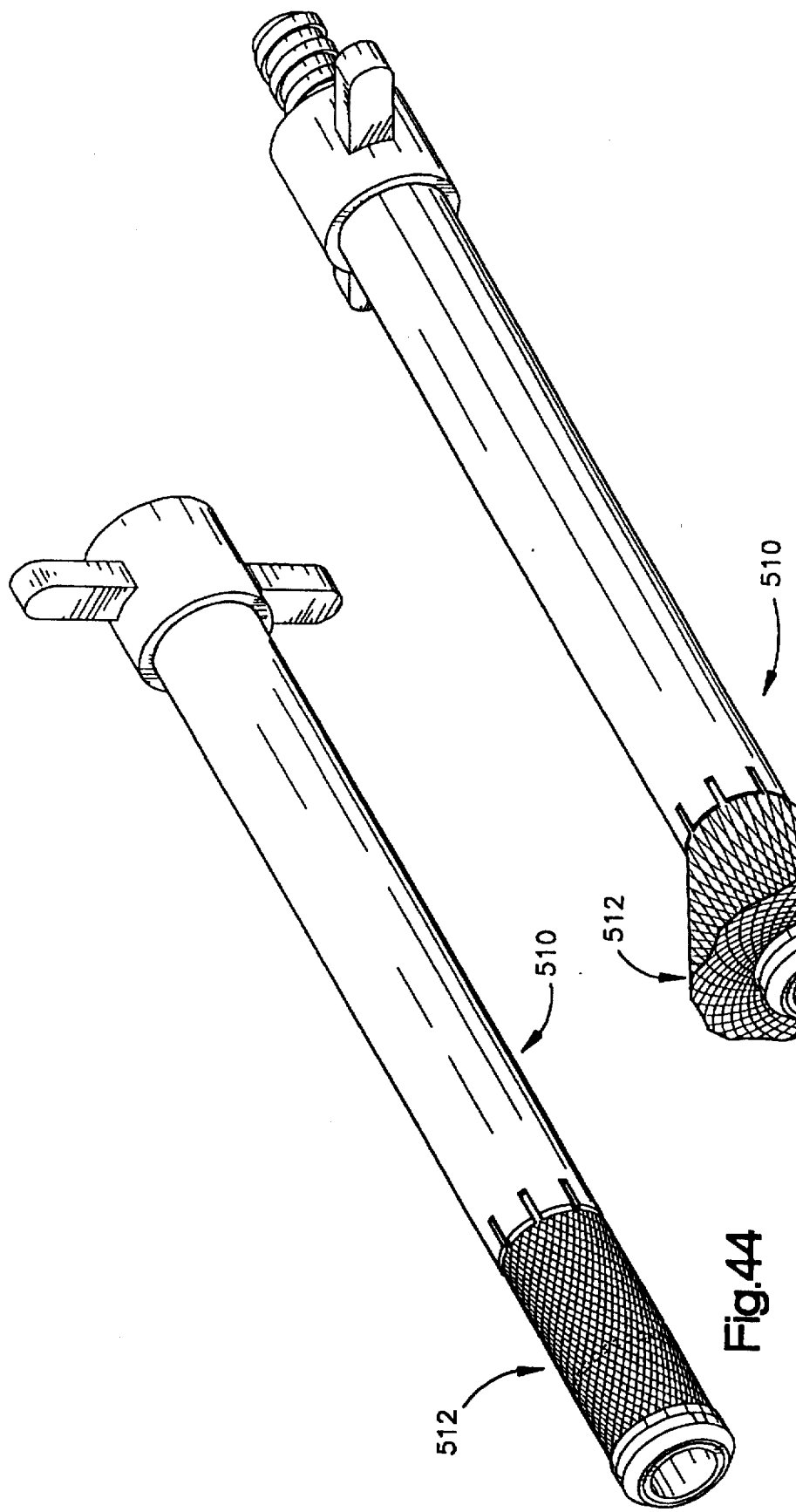

5,667,520

METHOD OF PERFORMING BALLOON DISSECTION

RELATED APPLICATIONS

This application is a division of and claims the benefit of copending application Ser. No. 08/029,695 filed Mar. 11, 1993. The aforementioned application Ser. No. 08,029,695 is itself a divisional of application Ser. No. 07/631,749, filed Dec. 18, 1990 (now U.S. Pat. No. 5,197,971). The aforementioned application Ser. No. 07/631,740 is itself a continuation-in-part of and claims the benefit of application Ser. No. 07/609,341, filed Nov. 5, 1990 (now abandoned). The aforementioned application Ser. No. 07/631,740 is also a continuation-in-part of and claims the benefit of the filing date of application Ser. No. 07/487,645, filed Mar. 2, 1990. The benefit of the earlier filing date of the aforementioned application Ser. Nos. 08/029,695; 07/631,740; 07/609,341; and 07/487,645 is claimed for all subject matter common to this application.

BACKGROUND OF THE INVENTION

The present invention relates to expandable subsurface devices for use in surgery. More particularly, the present invention relates to selectively expandable retractors for use in selectively and specifically moving sub-surface tissue in arthroscopic surgery, endoscopic surgery and fiber optic surgery. (The term "arthroscopic surgery" as used in this application includes endoscopic surgery, fiber optic surgery, and any other type of surgery on sub-surface tissues. Such surgery is performed percutaneously through a small incision or opening in the skin, as opposed to open surgery in which the surgeon cuts through and opens up all superior tissue until all the operating area is exposed.)

Arthroscopic surgery is currently performed without suitable tools for specifically moving tissue and creating visualization and working spaces. Generalized expansion is obtained with $CO_2$, $H_2O$, etc. However, this technique leaves fluid everywhere and is not useful to specifically move tissue.

There are no devices available which allow a surgeon to selectively position various tissue masses encountered during arthroscopic surgery. Delicate tissue such as nerve tissue or blood vessels is put at risk and can be damaged during an operation. Furthermore, the limited space available for the surgeon to work in could make an operation more difficult than it could be.

Retractors designed for use in open surgery are unusable in arthroscopic surgery. Current bladder devices such as a Foley catheter or those used in percutaneous transluminal coronary angioplasty are not useful to retract tissue in arthroscopic surgery, because they are made of a soft, pliable, flimsy material; they work with relatively low pressure; and they have smooth walls and a large surface area of contact so as not to damage the delicate tissues. Such bladder devices also inflate into a nonspecific shape, assuming the shape of whatever surface or object they encounter. They do not expand or retract at or near the tip, are not rigid enough to be insertable within a joint or among muscles, tendons and bones, and are too flexible to permit specific tissue retraction. Bladders can also be perforated during surgery.

Such bladder devices also do not provide enough force to move tissue as needed in arthroscopic surgery, mainly because they are designed to dilate an existing stretchable space within the body, such as a blood vessel, and not to create an actual space from a potential space such as in the subacromial bursa or carpal tunnel. In contrast, a great deal more force is needed to selectively move tissues such as muscles, bones, and tendons and expand a potential space therein. One must have a strong, sufficiently rigid instrument to do this, and exert much more force and yet protect delicate tissues. One also needs the ability to specifically direct force in specific locations or directions, not merely randomly. A bladder such as a Foley catheter would deform in an uncontrolled fashion, not pushing where it is needed most.

Accordingly, there exists a need for instruments suitable to mechanically specifically move tissue, which are small enough to fit through a small opening in the skin and which expand to create a working and visualization space in sub-surface tissues. Such instruments must be strong enough and precise enough for use in arthroacopic surgery. My co-pending applications identified above disclose devices suitable for such applications. This application is based on those applications and devices.

SUMMARY OF THE INVENTION

The present invention is a mechanically and pneumatically expandable retractor suitable for arthroscopic surgery and removable thereafter without significantly damaging the moved or retracted tissue. The retractor has a distal end and a proximal end. The retractor includes a mechanical expanding portion for expanding against sub-surface tissues when the retractor is in use, and a fluid-operated expanding portion for expanding against sub-surface tissues when the retractor is in use. The fluid-operated expanding portion can be axially co-extensive with the mechanical expanding portion of the retractor, or it can be placed elsewhere along the length or at the tip of the retractor. The fluid-operated expanding portion can expand either independently of or in conjunction with the mechanical expanding portion of the retractor.

The retractor preferably has a rigid shaft to allow the surgeon to apply force to sub-surface tissues by pulling or pushing on the retractor, or by using it as a lever. Alternatively, the shaft can be flexible, allowing the retractor to be positioned around a curve or corner and allowing the surgeon to pull back on the retractor to move tissue thereby.

In an alternative embodiment, the bladder is not fluid-expanded, but rather covers the mechanical expanding portion to separate it from tissues it contacts.

The retractor may have one or more central passages to function as a cannula. Alternatively, the retractor can be solid or needle-like with or without a removable trocar.

The retractor is contracted after use and removed from the body tissues without having significantly damaged the tissues.

The retractor provides the surgeon with the ability to selectively move or retract tissue and to expand a specific space, and to gain a visualization and working space, a function which is not available in present operating instruments.

BRIEF DESCRIPTION OF THE DRAWINGS

Further features of the present invention will become apparent to those skilled in the art to which the present invention relates from reading the following specification with reference to the accompanying drawings, in which:

FIG. 1 is a view of a cannula type retractor in accordance with the present invention, having a plurality of expanding arms, shown in an unexpanded condition;

FIG. 2 illustrates the retractor of FIG. 1 in an expanded condition;

FIG. 3 is a side elevational view of the body of the retractor of FIG. 1;

FIG. 4 is a longitudinal sectional view of the nut of the retractor of FIG. 1;

FIG. 5 is a side elevational view of the sleeve of the retractor of FIG. 1;

FIGS. 6A–H, J and K are a series of views illustrating the retractor of FIG. 1 and similar retractors in an expanded condition;

FIG. 7 is a view of a retractor having two axially spaced expanding portions, shown in an unexpanded condition;

FIG. 8 illustrates the retractor of FIG. 7 in an expanded condition;

FIG. 9 is a view of a retractor in accordance with the present invention, and also having an expandable bladder, shown in an unexpanded condition;

FIG. 10 illustrates the retractor of FIG. 11 in an expanded condition;

FIG. 11 is a view showing a retractor being used in carpal tunnel surgery, in an unexpanded condition;

FIG. 13 is a view similar to FIG. 11 with the retractor in an expanded condition;

FIG. 15 is a view of a non-cannula type retractor in accordance with the present invention, shown in an unexpanded condition;

FIG. 16 illustrates the retractor of FIG. 15 in an expanded condition;

FIG. 17 is an illustration of the use of a pair of retractors in arthroscopic shoulder surgery, with the retractors shown in an unexpanded condition;

FIG. 18 is an illustration similar to FIG. 17 with the retractors shown in an expanded condition;

FIG. 19 is a view of an elliptically shaped mechanical retractor, in an unexpanded condition;

FIG. 20 shows the retractor of FIG. 19 in an expanded condition;

FIG. 21 is an end view of the retractor of FIG. 20;

FIG. 22 is a view of a mechanical retractor with an independently operable pneumatic bladder retractor, both at the distal end, in an unexpanded condition;

FIG. 23 shows the retractor of FIG. 22 in an expanded condition;

FIG. 24 is an end view of the retractor of FIG. 20;

FIG. 25 illustrates a retractor having a pair of axially spaced expanding portions each being mechanically and pneumatically expandable;

FIG. 26 is an end view of the retractor of FIG. 25;

FIG. 27 is a view of a mechanical retractor with an independently operable pneumatic bladder retractor at a separate axial location, in an unexpanded condition;

FIG. 28 shows the retractor of FIG. 27 in an expanded condition;

FIG. 29 is a view of a mechanical retractor with an independently operable pneumatic bladder retractor disposed therein, in an unexpanded condition;

FIG. 30 shows the retractor of FIG. 29 in an expanded condition;

FIGS. 31A–H and J illustrate a variety of shapes for the pneumatically expandable retractor portion;

FIG. 32 is a view of a mechanical retractor having a pneumatic bladder as the motive force for expansion, in an unexpanded condition;

FIG. 33 shows the retractor of FIG. 32 in an expanded condition;

FIG. 34 is a view of another mechanical retractor having a pneumatic bladder as the motive force for expansion, in an unexpanded condition;

FIG. 35 shows the retractor of FIG. 34 in an expanded condition;

FIG. 36 is a view of mechanical retractor for separating tissue having a pneumatic bladder as the motive force for expansion, in an unexpanded condition;

FIG. 37 shows the retractor of FIG. 36 in an expanded condition;

FIG. 38 is a view of a pneumatic bladder retractor with mechanical arms, in an unexpanded condition;

FIG. 39 shows the retractor of FIG. 38 in an expanded condition;

FIG. 44 illustrates a mechanical retractor with a mesh-type non-pneumatic bladder secured to a mechanical expanding portion, in an unexpanded condition;

FIG. 45 shows the retractor of FIG. 44 in an expanded condition;

DESCRIPTION OF PREFERRED EMBODIMENTS OF THE INVENTION

Figure 12:
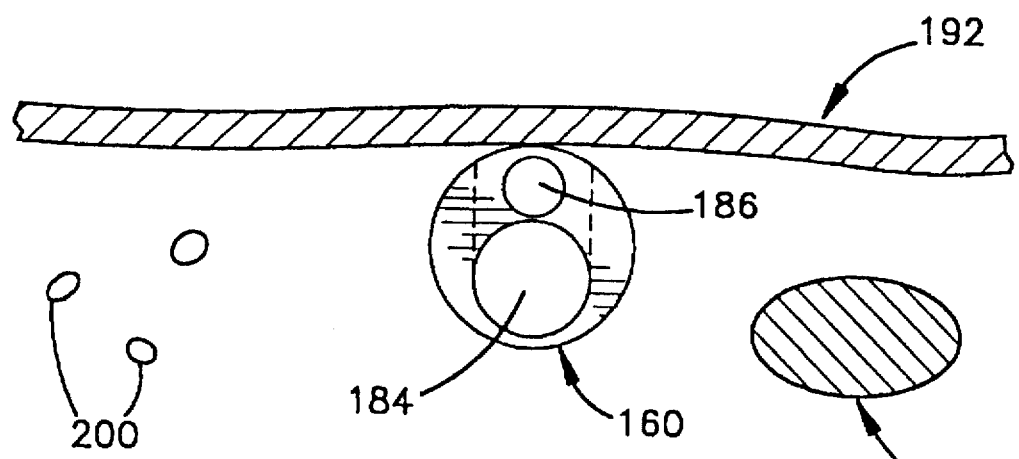
FIG. 12 is a simplified transverse sectional view of the operating area of FIG. 11.

By way of example, FIGS. 1–5 illustrate an arthroscopic retractor 10 in accordance with the present invention. The retractor 10 includes a retractor body 12, a retractor sleeve 14 and a nut 16.

The hollow tubular retractor body 12 (FIG. 3) includes a central portion 18, a widened distal end portion 20, and a threaded proximal end portion 22. The distal end portion 20 is of a larger diameter than the remainder of the retractor body 12. A pair of diametrically opposed notches 24, only one of which is seen in FIG. 3, are formed in the distal end portion 20. A central passage 26 extends longitudinally the entire length of the retractor body 12. The passage 26 is large enough for arthroscopic surgical instruments to pass through. The central portion 18 is rigid to allow manipulation of the distal end portion by moving the proximal end portion. Alternatively, the central portion could be flexible for easier positioning in the body. The threaded proximal end portion also includes suitable means (not shown) such as a clamp to hook up arthroscopic instruments, or to lock the retractor 10 on to such a device.

The nut 16 (FIG. 4) includes a body portion 30 having a threaded bore 32 for receiving the threaded end portion 22 of the retractor body 12. The nut 14 is enlarged to form a pair of handles 34 which extend from the body portion 30 of the nut 16. The handles 34 can be grasped by a surgeon to rotate the nut 16, and to manipulate the retractor 10 as a whole. An annular slot 36 is formed in the distal end portion of the nut 16.

The hollow tubular retractor sleeve 14 (FIG. 5) includes a central portion 40, a proximal end portion 42, and a distal end portion 44. The proximal end portion 42 has an oblong widened portion 46 which is received in the slot 36 in the nut 16. The distal end portion 44 has a pair of diametrically opposed projections 48, only one of which is shown in FIG. 5. The projections 48 are received in the notches 24 in the distal end portion 20 of the retractor body 12. A central passage 50 extends longitudinally through the entire length of the retractor sleeve 14. The passage 50 is sized to receive the central portion 18 and the proximal end portion 22 of the retractor body 12. The central portion 40 is rigid to allow manipulation of the distal end portion by moving the proximal end portion. Alternatively, the central portion could be flexible for easier positioning in the body.

The retractor sleeve 14 also includes an expanding portion 60. The expanding portion 60 includes a plurality of circumferentially spaced expanding arms 62. Adjacent arms 62 define between them a series of slots 64. The expanding portion 60 illustrated in the embodiment of FIGS. 1-5 has eight equally spaced arms 62 over a 360° range. It should be understood that the present invention contemplates that any different number of arms can be used, and they can be spread equally or unequally over a different circumferential extent, in order to provide varying or eccentric expansion.

Each expanding arm 62 extends between a groove 66 adjacent the distal end portion 44 of the sleeve 14, and a groove 68 adjacent the central portion 40 of the sleeve 14. The grooves 66 and 68 are formed on the exterior of the material of the sleeve. An intermediate groove 70 is formed on the interior of each arm 62 and divides each arm 62 into a distal expanding portion 72 and a proximal expanding portion 74. The grooves 66, 68, and 70 weaken the material of the sleeve 14. When force is directed axially on the distal end portion 44 of the sleeve 14 in a direction toward the proximal end portion, the material of the sleeve 14 buckles at the weakened areas of the grooves 66, 68, and 70, causing the arms 62 to expand radially outwardly.

To assemble the retractor 10, the hollow sleeve 14 is slid axially over the proximal end portion 22 of the body 12. The distal end portion 44 of the sleeve 14 engages the widened distal end portion 20 on the body 12. The projections 48 on the sleeve 14 engage the notches 24 on the body 12, blocking rotation of the sleeve 14 relative to the body 12. (Other structures can be used to obtain this blocking function. For example, if the retractor parts are injection molded, a key and keyway structure may be used for ease of manufacture.) At least a portion of the threaded proximal end portion 22 of the body 12 is exposed. The nut 16 is threaded onto the exposed proximal end portion 22 of the body 12. The widened portion 46 of the sleeve 14 is received in the slot 36 in the nut 16.

To operate the retractor 10, the nut 16 is rotated on the threaded proximal end portion 22 of the body 12, decreasing the distance between the nut 16 and the distal end portion 20 of the body 12. The sleeve 14 is compressed axially. The sleeve 14 buckles at the grooves 66, 68, and 70. The arms 62 on the sleeve 14 move radially outwardly from an unexpanded condition as shown in FIG. 1 to an expanded condition as shown in FIG. 2. (Any system for shortening the sleeve other than a threaded system can be used also.)

The radially outermost surface 78 of each expanded arm 62, which is the radially outermost point of the retractor 10, is located axially at the distal end of the retractor 10. Because the retractor 10 expands at its distal end, not at a mid-portion, stability is increased, since the surgeon is holding the retractor 10 at its proximal end and the retractor 10 is firmly positioned at its distal end. Also, the expanded retractor 10 thus creates a working space where the surgeon needs it, without having to go further down with the instrument as would be necessary if the expanding portion were axially centrally located. The retractor 10 is rigid in a transverse direction, and therefore the surgeon can pull push or lever it to manipulate subcutaneous tissue.

There are a variety of ways in which the expanding portion of a retractor in accordance with the present invention can be configured for particular surgical applications. In the retractors shown in FIG. 6, the expanding arms 62 are disposed irregularly circumferentially around the retractor to provide an increased working space or operating area between particular pairs of expanding arms 62. The external shape of the retractor when expanded, and the amount of expansion, are designed for the specific application on which that retractor is to be used. For example, if the surgeon is working against bone, he can select a retractor which is configured so that it stays flat against the bone, and expands away in the opposite direction, to push tissue away from the bone and create a working and visualization space next to the surface of the bone.

The retractor of the present invention, therefore, is not merely a round structure which expands. It allows mechanical manipulation of tissue, a function which is not available now in arthroscopic surgery. It can be in the shape of an umbrella; oval; wedge; cone; triangular; I-beam; a half-moon shape to protect a nerve; a V-shape to push a nerve in a different direction; a V-shape which expands at the tip; T-shaped or L-shaped; or other shapes as desired.

As an example, the retractor 10a (FIG. 6) includes a sleeve 14a similar to the sleeve 14 of the retractor 10, but with one less expanding arm. An enlarged working space 81 is formed between the arm 82 and the arm 84 of the sleeve 14a. A greater portion of the retractor body central portion 18 is thus exposed.

Similarly, the retractor 10b includes a sleeve 14b having six expanding arms. A larger working space 85 is created between the arms 86 and 88, exposing a larger portion of the body central portion 18. In the retractor 10c, the sleeve 14c has only five radially expanding arms, creating a 180° working space 89 between the arms 90 and 92.

In the retractor 10d, six expanding arms are spaced circumferentially around the sleeve 14d to expose the retractor body central portion 18 on opposite sides. A working space 93 is created between the arms 94 and 96 on one side, and a working space 97 is created between the arms 98 and 100 on the opposite side. In the retractor 10e, only four expanding arms are present, and even larger working spaces are created on opposite sides, that is, a space 101 between the arms 102 and 104 on one side, and a space 105 between the arms 106 and 108 on the opposite side.

It can thus be seen that the retractor 10 can be configured to meet almost any application, by appropriately locating and sizing and configuring the expanding portion of the sleeve 14 of the retractor. For example, there may be provided longer expanding arms to provide for a greater amount of expansion. The arms may in such a case may be made thicker for greater strength. All such configurations are included within the scope of the present invention.

Also included are structures functionally equivalent to the expanding arm construct. For example, the expanding portion of a retractor in accordance with the present invention may be as simple as an expansion device like a screw jack or an inflatable bladder disposed between two opposed plates which spread apart upon actuation of the expansion device. A cable can be used to pull on a part to cause expansion. Or, a cam-operated mechanism can be used with a sliding or rotating part to cause expansion.

The central passage 26 through the body portion of the retractor 10 effectively allows the retractor 10 to serve as a cannula through which surgical instruments can be passed even when the retractor is in use. If a side portal is provided in the retractor as described below, surgical instruments, tools, fluid lines, etc. can be passed into or out of the retractor through the side portal.

Another important feature of the retractors of the present invention is that they can be contracted after use of the retractor to allow the retractor to be removed from the operating area. The structure of the retractor allows for safe decompression (contraction) and removal of the device after use. For example, in the retractor illustrated in FIGS. 1-5, the widened portion 46 of the retractor sleeve 14 is received in the slot 36 in the nut 14. After expansion of the sleeve as described above, when the nut 14 is rotated back so as to move away from the distal end portion 20 of the retractor body 12, the nut 14 pulls the widened portion 46 of the sleeve 14, lengthening the sleeve and causing the arms 62 to contract to their starting (unexpanded) position. The retractor 10 can then be removed easily from the operating site, without having significantly damaged any tissue. This feature is not available with any previous mechanical expanding devices such as expanding bone screws.

FIGS. 7 and 8 illustrate another embodiment of the invention in which a retractor 110 includes two separate axially spaced expanding portions and also has a side portal through which an arthroscope and/or other arthroscopic surgical instruments may be passed.

The retractor 110 includes a hollow retractor body 112 having a distal end portion 114 with a tool hole 116 and a scope hole 118. An edge 120 defines an opening or side portal 122 in the retractor body 112. The opening 122 communicates with a central passage extending axially through the body 112.

The hollow tubular retractor sleeve 124 includes an intermediate portion 126, a pair of expanding portions 128 on either side of the intermediate portion 126, and a proximal sleeve portion 130. Each expanding portion 128 of the sleeve 124 includes a plurality of arms 62 similar to the expanding arms 62 in the embodiment illustrated in FIGS. 1-5. Each circumferentially aligned pair of arms 62 is connected by an intermediate sleeve segment such as the segments 125 and 127. In the retractor 110, the expanding arms 62 are spaced circumferentially about the sleeve 14 so that the space between the intermediate segments 125 and 127, as well as the space between adjacent arms 62, is aligned with the opening 122 in the retractor body 112.

Accordingly, when the retractor 110 is expanded as illustrated in FIG. 8, there is access from the central passage of the retractor body 112, through the opening 122, and between adjacent intermediate segments and adjacent expanding arms, for the passage of surgical instruments. Furthermore, the pair of expanding portions 128 move tissue out of the way at axially spaced locations along the retractor 110, to provide a large working area extending longitudinally between the two expanding portions 128 of the retractor. In similar fashion, expanding portions like or similar to the expanding portions 128 can be placed at selected locations along a retractor in accordance with the present invention, in order to selectively retract tissue for a particular application. Two or more separate retractors can also be used for this function.

In another embodiment of the invention, an inflatable bladder is included on the mechanically expandable retractor. The bladder can be co-extensive with the expanding portion of the retractor, or it can be spaced apart from the expanding portion of the retractor. The bladder can be used independently or in conjunction with the mechanical retractor.

FIGS. 9 and 10 illustrate an embodiment of the invention which includes an inflatable bladder circumscribing the expanding portion of the retractor. A retractor 140 includes a sleeve 14 with an expanding portion 60 including a plurality of expanding arms 62. The body portion of the retractor 140 has a pointed distal end 142 for easier passage through tissues. Proximal to the threaded portion 22 of the retractor body, a portion 144 of the retractor includes a fluid supply port 146. An inflatable bladder 150 is bonded to the retractor sleeve 14 at two circumferential, axially spaced locations 152 and 154. Appropriate fluid passages are provided in the retractor body and the retractor sleeve to provide fluid communication between the fluid supply port 146 and the bladder 150. The bladder can be deflated with suction.

The bladder 150 inflates and expands radially upon the introduction of fluid under pressure into the fluid supply port 146. The bladder 150 can be inflated independently of expansion of the expanding portion 60 of the retractor 140. Alternatively, the bladder 150 can be expanded in conjunction with expansion of the expanding portion 60 of the retractor 140, in which case it may be preferable to have the bladder in the shape of the mechanical retractor.

The bladder 150 prevents tissue from being caught in between the expanding arms 62 to minimize tissue damage when the retractor is in use and to allow for easy contraction and removal of the retractor after use. The bladder 150 insures proper operation of the expanding portion 60 by keeping tissues out of its way to provide more uniform retraction. The bladder 150 has a tamponade effect, lessening bleeding in the surrounding tissues. The bladder 150 also spreads the retractive force, lessening the risk to delicate tissues such as nerve tissue.

An expandable bladder such as the bladder 150 can be provided at other locations along a retractor 140. For example, a bladder can be provided at a location spaced apart from any expanding portion of the retractor. Also, a bladder can be provided which spans longitudinally the distance between two expanding portions on a retractor. The bladder can be formed of a fluid tight material in order to maintain fluid pressure and exert greater force against the tissues of the body. The bladder can alternatively be made of a perforate material which allows fluid flow therethrough but which also serves to apply force against the tissue it encounters. The bladder may be reinforced, ribbed, or have a specific molded shape. The bladder may be constructed in accordance with my co-pending application Ser. No. 487,645, filed on Mar. 2, 1990, the disclosure of which is incorporated by reference. For example, the bladder is typically formed on a mandrel which is of a particular shape and which is sized about half way between the unexpanded and the expanded size of the bladder. The bladder may be thicker in some areas to expand less, and thinner in other areas to expand more. The bladder may have ridges or areas of differing degrees of resistance to stretching or flexing. The bladder can be pre-shaped to assume a certain form when expanded. The bladder can have a dual durometer layered construction, with a thin layer for fluid retention overlying a thicker layer for shaping. The bladder can have a bellows-type construction.

One basic purpose of the bladder on a retractor of the present invention is to maintain a separation between the expanding arms and the tissues they expand against. Therefore, the bladder need not be made of a fluid-tight material if the bladder per se is not to be expandable. If desired, the bladder can merely be a fabric, mesh, film, polymer, or other material extending over the expanding arms and moving radially outwardly with them. Whether the bladder is fluid-tight or not, the material of the bladder can be bonded directly to the arms. The material can be stretchable to expand when the expanding arms move radially outwardly then contract when the arms move back inwardly.

Use of only a bladder (without a mechanical retraction device) has the disadvantage that a bladder can be punctured with a surgical knife or cutter and will collapse, losing all the retraction gained upon inflation and possibly compromising the surgery. Because the retractors of the present invention are also mechanical in nature, this possibility is avoided, and secure retraction is provided.

FIGS. 11 through 14 illustrate the use of a retractor 160 in accordance with the present invention in carpal tunnel surgery. The retractor 160 is illustrated in FIGS. 11 and 12 in an unexpanded condition, and in FIGS. 13 and 14 in an expanded condition. The retractor 160 is inserted through an incision 190 in the wrist, and underneath the transverse carpal ligament 192, adjacent the median nerve 194 of a hand 196.

The retractor 160 includes an expanding portion 161 with a plurality of expanding arms 62, two of which are spaced about an opening or side portal 162 for instrument passage therethrough. An expanding bladder 164 is bonded to the sleeve 166 of the retractor 160. The retractor 160 is secured in a holder 170 having a pair of grips 172 and 174. The grip 172 is fixedly attached to a sleeve clamp 176 which securely clamps the sleeve 166 of the retractor 160. The grip 174 is fixedly attached to a portion 178 for engaging a widened portion 180 on the body portion 182 of the retractor 160. The body portion 182 has a scope hole 184 and a tool hole 186 extending therethrough. Suitable locking means can also be provided to lock the retractor in a particular expanded condition.

Figure 14:
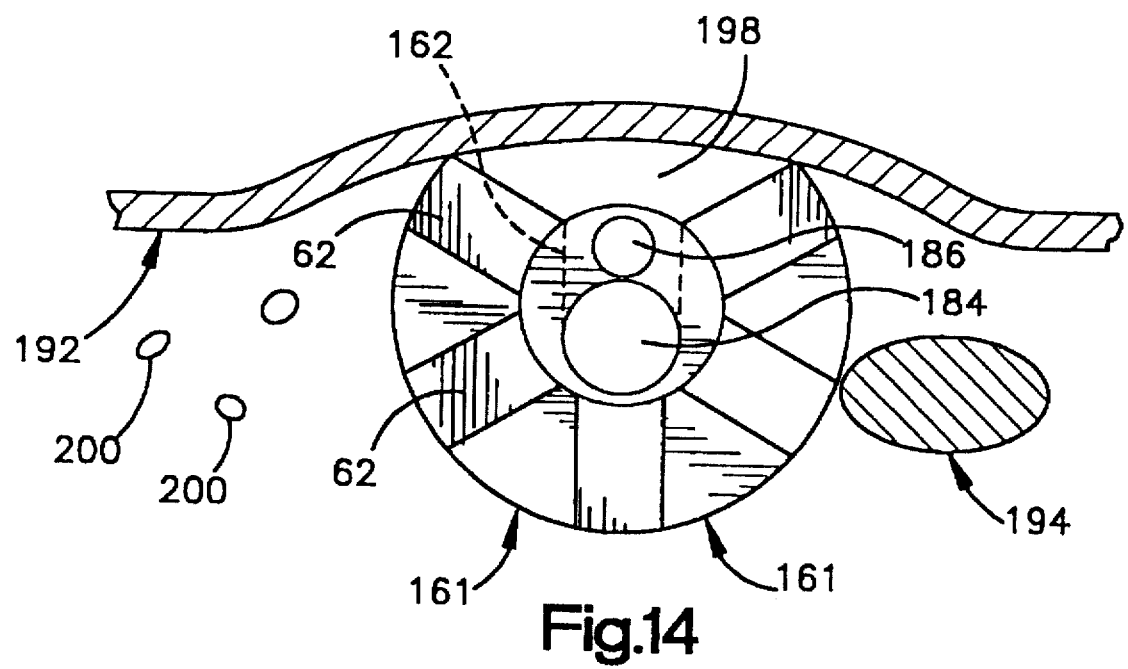
FIG. 14 is a simplified transverse sectional view of the operating area of FIG. 13.
Figures 40, 41:
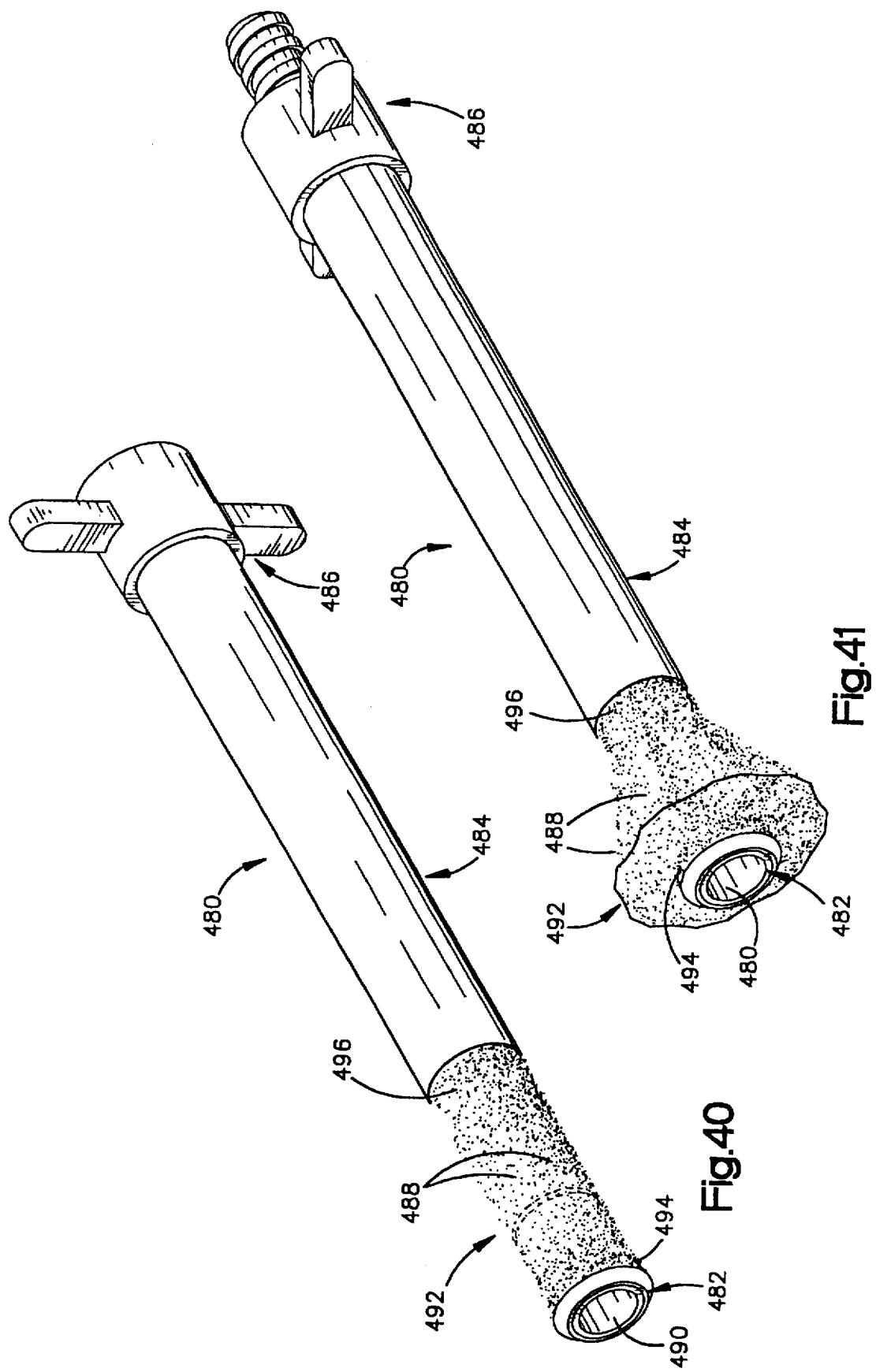
FIG. 40 illustrates a mechanical retractor with a non-pneumatic bladder secured to a mechanical expanding portion, in an unexpanded condition.
FIG. 41 shows the retractor of FIG. 40 in an expanded condition.
Figures 42, 43:
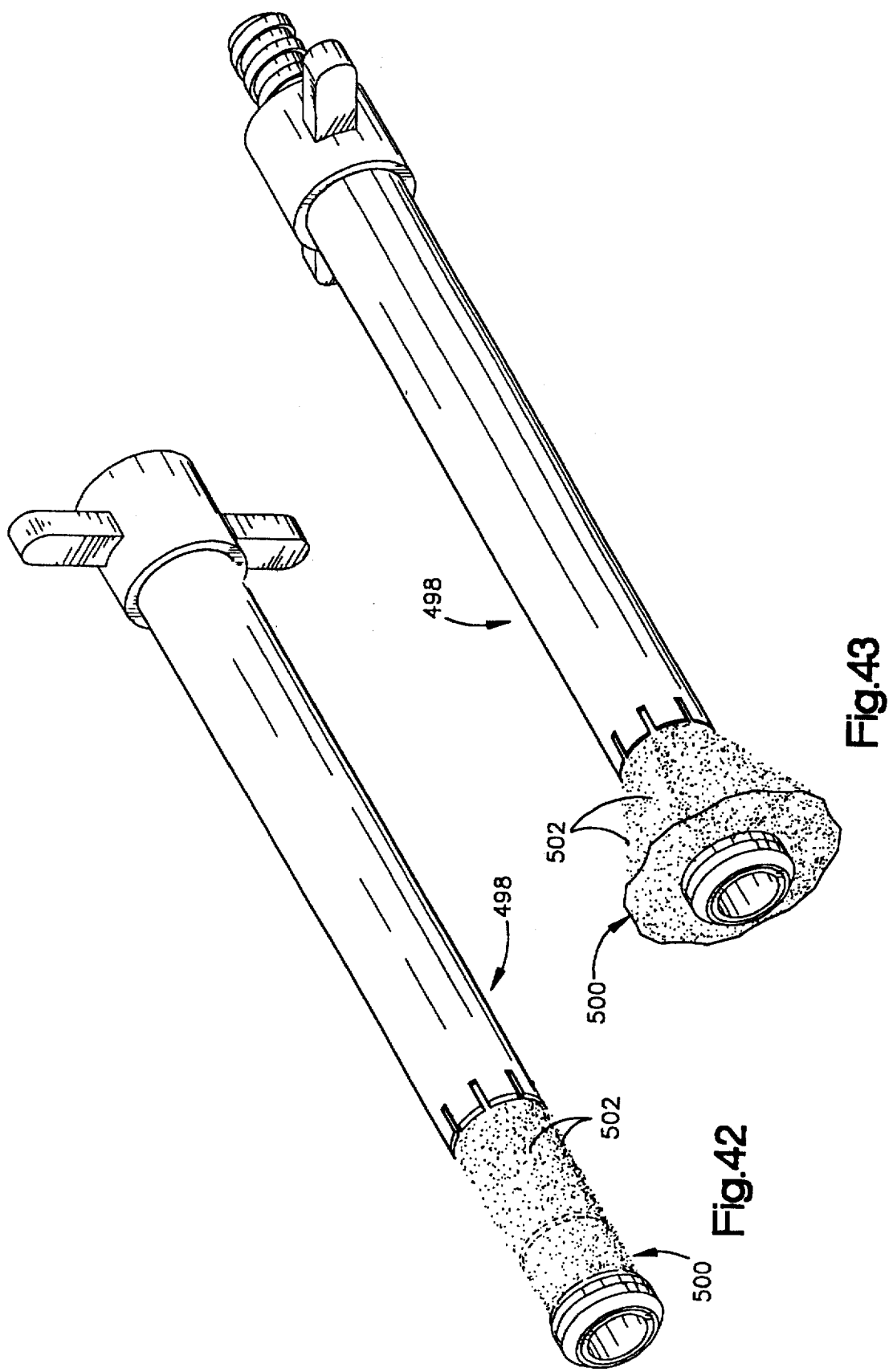
FIG. 42 illustrates another mechanical retractor with a non-pneumatic bladder secured to a mechanical expanding portion, in an unexpanded condition.
FIG. 43 shows the retractor of FIG. 42 in an expanded condition.

FIGS. 13 and 14 illustrate the retractor 160 in an expanded condition. Relative movement of the grip 172 toward the grip 174 draws the body portion 182 proximally relative to the clamped sleeve portion 166, expanding the expanding portion 161. The expanding arms 62 move radially outwardly to create a working or operating area 198 adjacent the ligament 192. The bladder 164 is also expanded about the expanding portion 60 of the retractor 160. Tissue is not significantly damaged by the retractor 160. After the operation is completed, the retractor 160 is simply contracted or collapsed and removed from the operating site.

Because of the controlled expansion of the retractor 160, the median nerve 194 is shielded from the operating area. Tools and an arthroscope may be passed through the opening 162 into the operating area 198, while the median nerve 194 and other tissues such as tendons 200 are safely shielded from the operating area 198. Accordingly, by use of the retractor 160, the surgeon is provided with an enlarged open area in which he can work on the ligament 192, and at the same time he has protected the median nerve 194 from the operating area. The surgeon has full visualization and working of the entire space, not a limited vision area as with other systems. This type of operation can, of course, be performed also with a mechanically expandable retractor not having a bladder thereon.

Indicated schematically at 193 in FIG. 11 is means for measuring the retractive force applied by the expanding portion of the retractor 160. This can be any suitable apparatus for measuring the force needed to bring together the grips 172 and 174, for example. With the retractor of FIGS. 1–5, a torque wrench or other instrument can be used to measure the force needed to turn the nut 16. Similarly, any known apparatus can be used to monitor the fluid pressure inside an expandable bladder on a retractor of the present invention. Thus, with any of the present retractors, the expansion force can be monitored and controlled.

FIGS. 15 and 16 illustrate another embodiment of the mechanically expandable retractors in accordance with the present invention. The retractor 210 illustrated in FIGS. 15 and 16 is a non-cannula type retractor. It does not have a central passage extending longitudinally through the retractor, but rather is solid or needle-like. Accordingly, the retractor 210 may be made slimmer if desired. It may be desirable to use such a non-canula type retractor in a situation where the surgeon is already employing a cannula through which instruments and/or a scope may be passed. The retractor may have a removable trocar also.

The retractor 210 may have a pointed distal end portion 212 for easier insertion through tissues. (Alternatively, the retractor may be utilized in conjunction with a removable trocar. The pointed distal end portion would be the distal tip of a removable trocar which would be removed after placement of the expanding portion of the retractor in the desired location.) The retractor 210 has an expanding portion 60 with a plurality of expanding arms 62. Grooves 66, 68, and 70 in the sleeve 14 define the arms 62 and provide weakened portions to allow for radial expansion of the arms 62. Rotation of the nut 16 relative to the threaded proximal end portion 22 of the retractor body 214, shortens the distance between the nut 16 and the distal end 212 of the retractor body. The sleeve 14 is compressed axially, and the arms 62 expand radially outwardly.

The expanding portion of the retractor 210 illustrated in FIGS. 15 and 16 is oriented in the opposite direction longitudinally from the expanding portion of the retractor shown in FIGS. 1–5. Thus, the maximum point of expansion is spaced from the distal end of the retractor 210. However, this configuration provides an annular end face 216 at the proximal end of the expanding portion 60. Thus, the retractor 210 is usable to pull back on tissue, or to hook tissue to move it proximally. The retractor shown in FIGS. 1–5 would in such use slide out because its expanding portion has a conical shape with an apex at its proximal end. This "reversed" design can be revised in practice to place the maximum point of expansion closer to or at the distal end of the retractor.

FIGS. 17 and 18 illustrate the use of a pair of retractors in accordance with the present invention to perform arthroscopic surgery on the acromion 220 in the shoulder. The humeral head 222 is spaced from the acromion 220, with the rotator cuff 224 and the bursa 226 therebetween. The bursa 226 normally fits tight up against the surface 228 of the acromion 220, but is shown spaced therefrom for clarity. Because the bursa 226 is normally tight up against the surface 228 of the acromion 220, it is difficult to operate on the surface 228 of the acromion 220.

To gain access to the surface 228, a pair of retractors 230 and 232 are used. The retractor 230 is inserted through an incision 234 in the back 236 of the shoulder. The retractor 230 has an expanding portion 238 located below the surface of the skin. The retractor 230 has a projecting portion 240 located above the surface of the skin. The retractor 230 has a passage 242 to allow the passage of surgical instruments therethrough.

The retractor 232 is inserted through an incision 242 in the side of the shoulder. An expanding portion 244 of the retractor 232 is located below the surface of the skin. A projecting portion 246 of the retractor 232 is located above or outside of the skin. The retractor 232 has a central passage 248 to allow the passage of an arthroscope therethrough.

The retractor 230 is inserted through the incision 234 until its expanding portion 238 engages the surface 228 of the acromion 220. The expanding portion 238 is irregularly configured so as to stay relatively flat against the acromion 220 and expand 180° away to push the bursa 226 away from the surface 228. The expanding portion 238 is then expanded. The bursa 226 and rotator cuff 224 are forced away from the surface 228, creating a working and visualization space 250 against the surface 228. Similarly, the retractor 232 is inserted through the incision 242 until its expanding portion 244 engages the surface 228. The expanding portion 244 is then expanded. The bursa 226 and the rotator cuff 224 are forced away from the surface 228, enlarging the working and visualization space 250.

An arthroscope is then inserted through the passage 248 in the retractor 232 until its distal end is located in the space 250. A shaver is then inserted through the passage 242 in the retractor 230, until its distal end is also in the working space 250. The surgeon thus has both the arthroscope tip and the shaver in a clear volume adjacent the surface to be worked upon. The surgeon can then remove an area of bone 252 from the acromion 220, without interference from the bursa 226 and the rotator cuff 224 which are normally tight up against the surface 228.

The surgeon can manipulate the projecting portion 240 of the retractor 230, and the projecting portion 246 of the retractor 232, to further move the tissues as desired. For example, the surgeon can pull proximally on the projecting portion 246 of the retractor 232 to pull the bursa 226 and rotator cuff 224 away from the surface 228. The surgeon can use the retractor 230 as a lever, moving the projecting portion 240 thereof upwardly as viewed in FIG. 18 to move the expanding portion 238 relatively downwardly to move the bursa 226 and the rotator cuff 224 away from the surface 228. Tissue is not significantly damaged by the retractor 230.

Upon completion of the operation, the expanding portion 238 of the retractor 230 is contracted or collapsed, and the retractor 230 is removed from the operating site. The expanding portion 244 of the retractor 232 is contracted or collapsed, and the retractor 232 is removed from the operating site. The bursa 226 and the rotator cuff 224 regain their original position against the acromion 220.

In accordance with a feature of the present invention, a retractor in accordance with the present invention need not have a round shape as shown in the drawings. Because there is no relative rotation between the retractor body and the retractor sleeve, neither must be round, and the body and sleeve need not have the same cross-sectional configuration. For example, the retractor may have an elliptical or oblong shape if two cannulas or passages are formed therein. The shape may be flattened if a slimmer profile is needed to pass between certain tissue layers. A square cross-section may be provided if desired. This ability to use any shape provides more leeway in configuring the expanding portion of the retractor, because the expanding portion does not have to have a round cross-sectional configuration.

In accordance with another feature of the present invention, a retractor can also function as two or more cannulas side-by-side. In those Figures which illustrate a cannula-type retractor having both a tool hole and a scope hole at the distal end, the tool hole and the scope hole are the ends of longitudinally co-extensive passages extending through the retractor body. These passages or lumens serve as two cannulas.

As an example of these two features, FIGS. 19–21 illustrate a mechanical retractor 260 with an elliptical cross-section and a dual-cannula configuration. The retractor 260 has a pair of passages 262 and 264 extending longitudinally through the retractor. The retractor 260 has an expanding portion 266 with a plurality of expanding arms 268. Grooves 270, 272, and 274 in the retractor sleeve 276 define the arms 268 and provide weakened portions to allow for radial expansion of the arms 268. When the sleeve 276 is compressed axially the arms 268 expand radially outwardly from the unexpanded condition shown in FIG. 19 to the expanded condition shown in FIG. 20.

FIGS. 22–24 illustrate an embodiment of the invention in which a plurality of inflatable bladders are located at the distal end portion of a retractor having a mechanical expanding portion. The retractor 280 has a sleeve portion 282, a body portion 284, and a nut 286 with handles 288 thereon. The retractor sleeve 282 includes a pair of expanding arms 290 on one circumferential side of the sleeve 282, and a pair of expanding arms 292 on the opposite side. Located circumferentially between the arms 290 and the arms 292 are a pair of expanding bladders 294 and 296. The bladders 294 and 296 are supplied with fluid under pressure through a fluid supply line 298. A central passage 300 extends through the retractor 280.

The bladders 294 and 296 may work independently of the mechanical expansion of the retractor 280. The arms 290 and 292 are expanded by rotation of the nut 286 relative to the body portion 284, in a manner as described above. The bladders 294 and 296 are inflated upon the introduction of fluid under pressure through the fluid supply line 298. Such expansion is controllable independently of the expansion of the arms 290 and 292. Accordingly, the retractor 280 includes both mechanical and pneumatic expansion means, which are independently controllable, located at the same axial location along the retractor 280. The relative configurations of the bladders and of the mechanical expanding arms can be varied to suit the particular application for which any given retractor is used.

FIGS. 25 and 26 illustrate a retractor 302 having two expanding portions 304 and 306 spaced axially apart from each other. Each expanding portion 304 and 306 includes a plurality of mechanically expanding arms 308 of the type described above. A plurality of inflatable bladder segments 310 are interleaved between the arms 308. A scope hole 312 and a tool hole 314 extend through the body 316 of the retractor 302 and are accessible through a side portal 318. The side portal 318 is accessible through an opening 320 between adjacent intermediate sleeve sections 322 and 324 of the retractor sleeve 326. There is no bladder between the mechanical expanding arms 308 attached to the intermediate sleeve sections 322 and 324. Thus, a working area 328 (FIG. 26) is created which is accessible to the interior of the retractor 302 and from which tissue which has been pushed aside upon expansion of the retractor 302.

FIGS. 27 and 28 illustrate a retractor 332 having an inflatable bladder portion spaced axially from a mechanically expandable portion. The retractor 332 includes a sleeve 334 and a body 336. The sleeve 334 has an expanding portion 338 and an intermediate portion 340. A circumferentially extending bladder 342 is disposed at the distal end of the body 336. The bladder 342 extends most of the way about the circumferential extent of the sleeve 334, but does not cover a portion on which is formed a side portal 344 in the sleeve 334. The bladder 342 is inflatable or expandable independently of the mechanical expanding portion 338. Simultaneous expansion of both the bladder 342 and the expanding portion 338 creates a longitudinally extending working space between them, generally coextensive with the intermediate portion 340 of the sleeve 334. This working portion can be accessed through the side portal 344. It should be noted that, in another configuration, the position of the mechanical expanding portion 338 and the pneumatic expanding portion 342 can be reversed. It should also be noted that more than two expanding portions can be provided on one retractor. The number, configuration, and placement of the expanding portions can be varied in accordance with the particular application for that retractor.

FIGS. 29 and 30 illustrate a retractor 350 which includes a separate bladder that slides through the mechanical canula type retractor and is inflatable where needed at a location spaced apart from an expanding portion on the mechanical retractor. The retractor 350 includes a sleeve 352, a body 354, and a nut 356. An expanding portion 358 is located at the distal end of the sleeve 352, and a central passage 360 extends through the canula type retractor 350. A separate inflatable bladder 362 is disposed within the retractor 350, and can exit the distal end of the retractor 350 through an opening 364. The bladder 362 includes a fluid supply line 366 extending through the retractor 350. When expanded, the bladder 362 includes a widened portion 368 at its distal end 370, and a narrower conical portion 372 located proximal to the fluid supply line 366. The bladder 362 can be expanded simultaneously with the expanding portion 358, or can be expanded separately and independently as needed.

There are a variety of ways in which the pneumatic expanding portion (bladder) of a retractor in accordance with the present invention can be configured for particular surgical applications. The external shape of the bladder when expanded, and the amount of expansion, are designed for the specific application on which that retractor is to be used. For example, the bladder can extend only around a circumferential sector of the retractor, such as 90°, to provide an increased working space or operating area. Thus, if the surgeon is working against bone, he can select a bladder which is configured so that it stays flat against the bone, and expands away in the opposite direction, to push tissue away from the bone and create a working and visualization space next to the surface of the bone.

The bladder is therefore not merely a round structure which expands. It is configured to provide for selective mechanical manipulation of tissue, a function which is not available now in arthroscopic surgery. It can be in the shape of an umbrella; oval; wedge; cone; triangular; I-beam; a half-moon shape to protect a nerve; a V-shape to push a nerve in a different direction; a V-shape which expands at the tip; T-shaped or L-shaped; or other shapes as desired.

As an example, a retractor 374 (FIG. 31) includes a bladder 376 extending part way around the circumference of the retractor body 378. A central passage 380 extends through the retractor body 378 so that the retractor 374 can function as a cannula. Opposed axially extending surfaces 382 and 384 define a working space 386 between them.

Similarly, the retractor 388 includes a bladder 390 having opposed axially extending surfaces 392 and 394. A larger working space 396 is created between the surfaces 392 and 394, exposing a larger portion of the body portion 398. In the retractor 400, the bladder 402 has axially extending surfaces 404 and 406 which create a 180° working space 408 between the surfaces 404 and 406.

In the retractor 410, two expanding portions 412 and 414 are spaced circumferentially to expose the retractor body 416 on opposite sides. A working space 418 is created between the arms bladder surfaces 420 and 422 on one side, and a working space 424 is created between the bladder surfaces 426 and 428 on the opposite side. In the retractor 430, the axial orientation of the bladder 432 is reversed, so that it expands at its proximal end 434 rather than at its distal end 436. It can thus be seen that the bladder portion of a retractor of the present invention can be configured to meet almost any application.

In the retractors illustrated in FIGS. 32 through 37, an expandable bladder provides the motive force to separate two or more relatively rigid mechanical pieces. The mechanical pieces perform the actual tissue retraction.

The retractor 440 (FIGS. 32 and 33) includes a pair of jaws 442 and 444 pivotally mounted to a body portion 446. An expandable bladder 448 is disposed within the retractor 440 between the jaws 442 and 444. Upon expansion of the bladder 448, the Jaws 442 and 444 pivot radially outwardly from the position shown in FIG. 32 to the position shown in FIG. 33. This retractor configuration has several advantages. First, the jaws 442 and 444 expand most at their distal ends, as opposed to the more proximal expansion of the retractor of FIGS. 1–5, for example. Second, it can in some instances be easier to shape rigid mechanical pieces such as the jaws 442 and 444 to fit a particular application, than to shape an inflatable bladder.

The retractor 450 (FIGS. 34 and 35) includes a pair of jaws 452 and 454. The jaw 452 is fixed to the retractor body portion 456, and the jaw 454 is pivotally mounted to the body portion 456. An expandable bladder 458 is disposed within the retractor 450 between the jaws 452 and 454. Upon expansion of the bladder 458, the jaw 454 pivots radially outwardly from the position shown in FIG. 34 to the position shown in FIG. 35. This retractor configuration can be advantageous when it is desired to have expansion occur primarily on only one side of the retractor.

The retractor 460 (FIGS. 36 and 37) includes a pair of jaws 462 and 464. The jaw 462 is fixed to or integral with the retractor body portion 466. The jaw 464 is pivotally mounted to the pointed distal end 468 of the retractor 460. An expandable bladder 470 is disposed within the retractor 460 between the Jaws 462 and 464. The bladder 470 is secured to the inside of the jaws 462 and 464. The retractor 460 also includes means (not shown) for providing suction as well as inflation to the bladder 470. Upon expansion of the bladder 470, the proximal end of the jaw 464 pivots radially outwardly from the position shown in FIG. 36 to the position shown in FIG. 37. Upon the application of suction to the bladder 470, the jaw 464 pivots radially inwardly back to the closed position shown in FIG. 36.

The retractor 460 can be used as a wedge to separate tissue layers. The bladder 470 is first expanded to force tissue out of the way. The tissue stays apart for a period of time after being forced open. The bladder is then contracted with suction to bring the retractor to its closed condition. The pointed distal end 468 of the retractor 460 is then slid in further, and expanded again. The procedure is repeated as needed. Thus, the bladder is expanded and contracted to move tissue out of the way, and the retractor is gradually worked into the tissue to a depth that is required for the specific application.

In the retractor 472 (FIGS. 38 and 39), an inflatable bladder 474 is attached to an inner body portion 476 of the retractor 472. The bladder 474 is also attached to the insides of a plurality of expanding fingers 478. Upon inflation of the bladder 474, the fingers 478 move radially outwardly to move tissue as desired. The shape and amount of the expansion are controllable by not only the inflation of the bladder 474 but also the shape and size of the fingers 478. The greatest amount of expansion occurs at the distal end of the retractor.

On a retractor such as those shown in FIGS. 25 and 26, the bladder functions to separate the mechanical expanding arms and the tissues they expand against. Therefore, the bladder need not be made of a fluid-tight material if the expansion force is to be obtained solely mechanically. The bladder can merely be a fabric, mesh, film, polymer, or other material extending over the expanding arms and moving radially outwardly with them. The material of the bladder can be bonded to the body of the retractor or directly to the arms. The material can be stretchable to expand when the expanding arms move radially outwardly then contract when the arms move back inwardly.

These features are illustrated in the retractors shown in FIGS. 40–45. The retractor 480 (FIGS. 40–41) is configured mechanically like the retractor 10 shown in FIGS. 1–5. The retractor 480 includes a body portion 482, a sleeve portion 484, and a nut 486. The sleeve 484 has a plurality of expanding arms 488. A central passage 490 extends through the retractor 480 so that the retractor 480 functions as a cannula. A bladder 492 is bonded at 494 and 496 to the body 482 and the sleeve 484. The retractor 498 (FIGS. 42 and 43) is similar except that the bladder 500 thereon is bonded only to the expanding arms 502. In the retractor 510 (FIGS. 44 and 45), the bladder 512 thereon is formed of a fluid-permeable material such as an open-weave mesh-type fabric or other similar material which is biocompatible.

Figure 46:
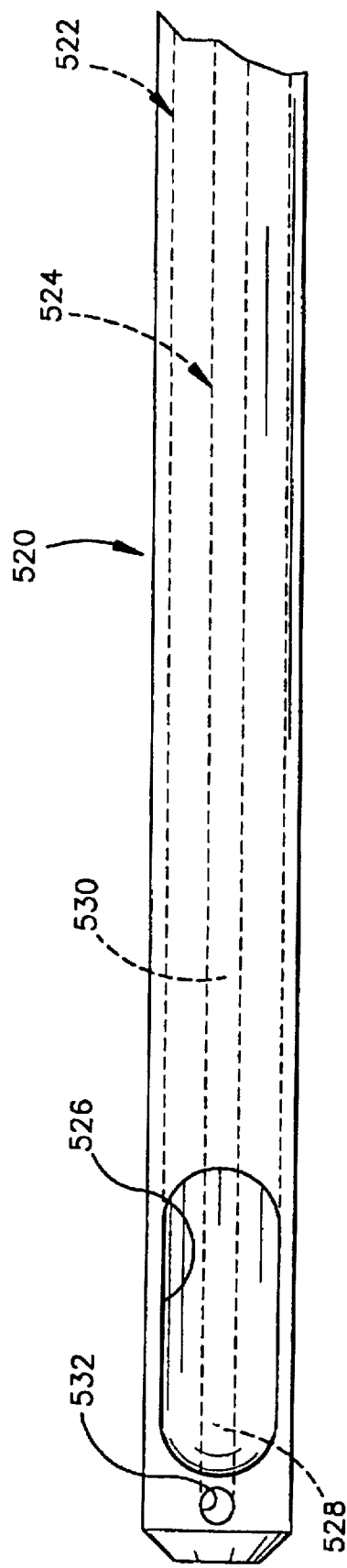
FIG. 46 is a top plan view of an apparatus for guiding an arthroscope and a cutting device.
Figure 47:
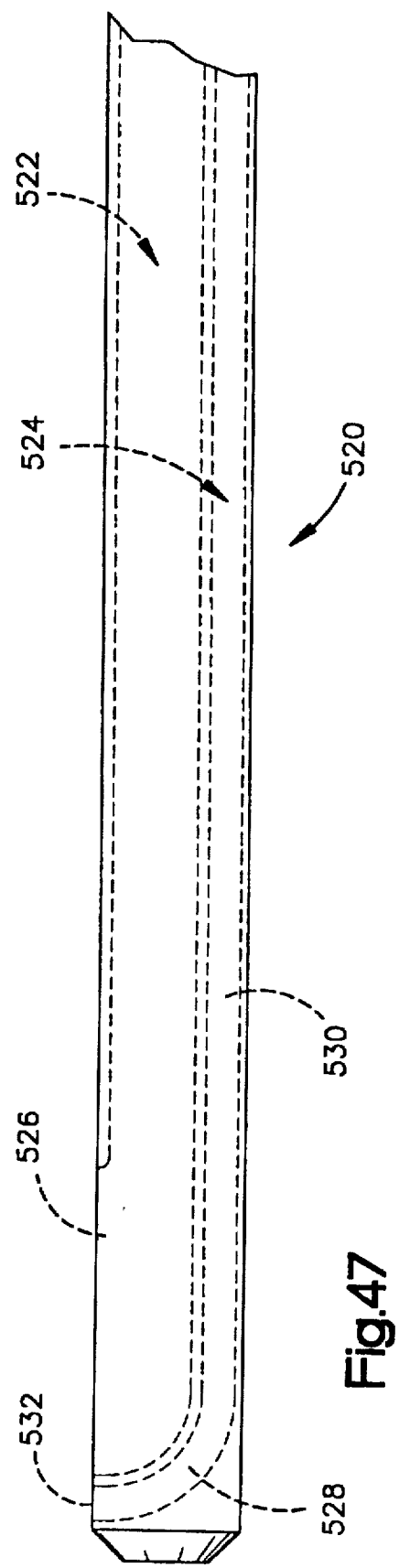
FIG. 47 is a longitudinal sectional view of the apparatus of FIG. 46.

FIGS. 46 and 47 illustrate a retractor body portion 520 which includes two parallel passages 522 and 524. The larger passage 522 is designed for the passage therethrough of an arthroscope. The smaller passage 524 is designed for the passage therethrough of a fiber optic laser cutter or electric cautery device. The passage 522 has a relatively long portal or opening 526, suitable for an arthroscope with a viewing angle of 10° or more. The end portion 528 of the smaller passage 524 extends at an angle to the main portion 530, and terminates in a relatively small portal or opening 532. Thus, a device inserted through the smaller passage 524 will exit the body portion 520 at an angle to its longitudinal extent.

This configuration is ideal for the above-described use of a fiber optic laser cutter or electric cautery device in conjunction with an arthroscope. The fiber optic laser cutter will cut at a location directly in front of and in the field of view of the arthroscope. Fiber optic laser cutters are available in sizes as small as 0.6 mm in diameter. The device 520 can be correspondingly small in overall size. If made of a plastic material, the device 520 electrically insulates the cutting device from the body tissues. Accordingly, the present invention provides structure ideally suited for enhanced arthroscopic cutting. Because the cutting device and the arthroscope are fixed in position relative to each other, the apparatus 520 allows direct control of both the arthroscope and the cutting device while controlling the location of the retractor.

It should be noted that the apparatus 520 illustrated in FIGS. 46 and 47 is suitable for use alone, that is, without the sleeve portion of the retractor. In this manner, the apparatus serves as an inserter or guide for the arthroscope and the cutting or cautery device. The apparatus can be fixed to the arthroscope to enhance stability. The tissue to be operated upon can be retracted with a separate arthroscopic retractor at the work area.

In each of these retractors, the bladder prevents tissue from being caught in between the mechanical expanding arms. This minimizes tissue damage when the retractor is in use, and allows for easy contraction and removal of the retractor after use. The bladder insures proper operation of the mechanical expanding portion by keeping tissues out of its way to provide more uniform retraction. The bladder also has a tamponade effect, lessening bleeding in the surrounding tissues. The bladder also spreads the retractive force, lessening the risk to delicate tissues such as nerve tissue.

In accordance with another feature of the present invention, the retractors incorporate a projecting portion at their proximal ends for manipulating the retractor. The projecting portion projects from the surface of the body tissues when the retractor is in use. In FIGS. 1–5, for example, the proximal end portion 22 of the retractor body 12 and the proximal end portion 42 of the sleeve 14, along with the nut 16, project from the surface of the body tissues when the retractor is in use. The retractor 10, when expanded, can thus be used to pull or push on tissue to move the tissue subcutaneously. Similarly, the retractor 160 illustrated in FIGS. 11 through 14 has parts projecting outwardly of the incision 190 to allow external manipulation of the sub-surface portion of the retractor.

This external projecting portion (or handle) is useful in many ways. It allows the surgeon to move tissues at will by pulling or pushing on the retractor or using it as a lever to move tissue subcutaneously. The surgeon can control the working point deep within the tissues because he can control the exposed portion of the retractor. Also, it allows the surgeon to block fluid flow, as an expanded retractor can be pulled back to seal flow and give more room to see and work. The retractor can also free up one hand for the surgeon.

These are all features which are available to a surgeon in open surgery, but not in arthroscopic surgery unless using a retractor as described herein. The intermediate portion of a retractor of the present invention is preferably rigid enough to provide for such manipulation and to provide for precise positioning of the expandable portion within the body tissues. Alternatively, the intermediate portion can be flexible or selectively rigidifiable.

A retractor in accordance with the present invention is small and light weight, and thus can be packaged under sterile conditions and be disposable to maintain sterility. Current retractors have been constructed which are about 85 mm long, about 7 mm across in an unexpanded condition, and about 26 mm across when expanded. The amount of expansion can be greater or less. The dimensions will vary significantly, of course, with the particular surgical application. For example, the expanding portion can be made smaller in diameter (when unexpanded) than the body portion of the retractor. In percutaneous (fiber optic or endoscopic) abdominal or thoracic surgery, expansion of up to 10 cm or more is needed, to move the stomach or small intestine, the greater omentum, the spleen, or the liver. The number and placement of expanding portions will vary with the application also.

Retractors have been constructed of polymers such as nylon, but can be injection molded of other materials also. Retractors can also be constructed of polymers, composites, and/or metals such as aluminum. The surface of the material can be pebbled or roughened or ridged, or have serrated edges, to better grip tissue and hold the retractor in position. Of course, the surface must still remain smooth enough so that the retractor is easily removable without damage to the tissue it contacts.

The various portions or the retractor can be made of different materials. The bladder, as mentioned, is preferably made of an elastomeric material which is strong enough to move tissue as desired. A suitable material for the expandable bladder 130 is Silastic® elastomer, which is available from Dow Corning in medical grades. The mechanical expanding portion can be made of nylon for light weight and sufficient strength. The shaft can be made of aluminum for rigidity.

The retractor also need not be straight as shown in the drawings. The retractor can be angled or bent, for example at a 45° or 90° angle, in the intermediate portion. Appropriate means for transmitting force at an angle are provided in such case in order to be able to shorten the sleeve to expand the arms.

Any part or all of the retractor can be made of a biodegradable material. For example, the mechanical expanding portion of a retractor can be made of a biodegradable material, and can be made detachable from the remainder of the retractor. Similarly, the expandable bladder can be made of a biodegradable material, and can be made detachable from the remainder of the retractor. In such a case, the biodegradable portion can be detached and left in the body after surgery. This is useful, for example, to prevent adjacent tissue planes from scarring together after surgery. The biodegradable mass will in time disappear, allowing the tissues to adjoin after they are healed.

The expandable portion 60 or the expandable bladder 130, or even the entire retractor, can be made of a transparent material to provide a better view of the operating area and improved visualization.

The amount of expansion of the retractors can be varied. Retractors of the present invention can be constructed which will expand up to 600% or more, and from as little as a few millimeters up to about ten centimeters or more, dependent on the location of use. This range of expansion is unattainable by any other available device.

From the above description of the invention, those skilled in the art will perceive improvements, changes and modifications. Such improvements, changes and modifications within the skill of the art are intended to be covered by the appended claims.

I claim:

1. A method of creating an anatomical space in body tissue by dissecting a first layer of tissue from a second layer of tissue along a natural tissue plane, said method comprising the steps of:

making an incision in the body which provides access to the natural tissue plane;

inserting a substantially rigid member having a bladder disposed on a distal portion thereof through said incision, said bladder being capable of exerting sufficient force when inflated to dissect the first layer of tissue from the second layer of tissue;

moving said member along the natural tissue plane to a location where it is desired to create the anatomical space between said first and second tissue layers;

inflating said bladder to dissect said first layer of tissue from said second layer of tissue along the natural tissue plane to create the anatomical space;

deflating said bladder;

moving said member to a new location between said tissue layers; and inflating said bladder again to cause farther dissection of said first and second layers of tissue and to enlarge the anatomical space.

2. A method as set forth in claim 1 wherein said substantially rigid member includes a pair of jaw members actuated by said bladder and wherein said step of inflating said bladder to dissect said first layer of tissue from said second layer of tissue includes pressing one of said jaw members against one of said layers of tissue under the influence of force applied against an inner surface of said one jaw member by said bladder.

3. A method as set forth in claim 1 wherein said substantially rigid member includes a jaw member and wherein said step of moving said substantially rigid member along a natural tissue plane to a location where it is desired to create the anatomical space between said first and second layers of tissue includes positioning said jaw member between said layers of tissue, and said step of inflating said bladder to dissect said first layer of tissue from said second layer of tissue includes pivoting said jaw member about an axis at a distal end portion of said substantially rigid member under the influence of force transmitted from said bladder to said jaw member as said bladder expands and pressing an outer side surface of said jaw member against one of said layers of tissue as said jaw member pivots about said axis at said distal end portion of said substantially rigid member.

4. A method as set forth in claim 1 wherein said substantially rigid member includes an axially tapered distal end portion and wherein said step of moving said substantially rigid member to a location where it is desired to create the anatomical space between said first and second tissue layers includes positioning said axially tapered distal end portion between said layers of tissue, said step of inflating said bladder to dissect said first layer of tissue from said second layer of tissue includes expanding said axially tapered distal end portion under the influence of force transmitted from said bladder to said end portion as said bladder expands and pressing an outer side surface area of said end portion against one of said layers of tissue.

5. A method as set forth in claim 4 wherein said step of deflating said bladder includes contracting said axially tapered distal end portion, said step of moving said substantially rigid member to a new location between said tissue layers includes moving said axially tapered distal end portion further into said layers of tissue with said axially tapered distal end portion contracted, and said step of inflating said bladder again to cause further dissection of said first and second layers of tissue includes again expanding said axially tapered distal end portion by moving said distal end portion under the influence of force transmitted from said bladder to said distal end portion as said bladder is again inflated.

6. The method of claim 1 wherein said substantially rigid member includes means for mechanically separating tissue, and wherein said steps of inflating and inflating said bladder again include utilizing said bladder to actuate said mechanical separating means.

7. The method of claim 1 further comprising the step of inserting a scope through the incision and viewing the creation of the anatomical space.

8. The method of claim 1 further comprising the step of performing a surgical procedure in the created anatomical space.

* * * * *

UNITED STATES PATENT AND TRADEMARK OFFICE
CERTIFICATE OF CORRECTION

PATENT NO. : 5,667,520
DATED : September 16, 1997
INVENTOR(S) : Peter M. Bonutti It is certified that error appears in the above-indentified patent and that said Letters Patent is hereby corrected as shown below:

In column 6, line 12, after "pull" insert therefor --,--;

In column 6, line 12, after "push" insert therefor --,--;

In column 7, line 2, delete "construct" and insert therefor --construction--;

In column 13, line 25, delete "canula" and insert therefor --cannula--;

In column 13, line 31, delete "canula" and insert therefor --cannula--;

In column 14, line 27, delete "Jaws" and insert therefor --jaws--;

In column 14, line 51, delete "Jaws" and insert therefor --jaws--;

In the claims, column 18, line 7, delete "farther" and insert therefor --further--.

Signed and Sealed this

Twentieth Day of January, 1998

Attest:

BRUCE LEHMAN

*Attesting Officer*    *Commissioner of Patents and Trademarks*